(12) United States Patent
Meier

(10) Patent No.: US 11,360,003 B2
(45) Date of Patent: Jun. 14, 2022

(54) APPARATUS AND METHODS FOR CONTROLLING ATTENTION OF A ROBOT

(71) Applicant: GoPro, Inc., San Mateo, CA (US)

(72) Inventor: Philip Meier, San Diego, CA (US)

(73) Assignee: GoPro, Inc., San Mateo, CA (US)

( * ) Notice: Subject to any disclaimer, the term of this patent is extended or adjusted under 35 U.S.C. 154(b) by 214 days.

(21) Appl. No.: 16/743,095

(22) Filed: Jan. 15, 2020

(65) Prior Publication Data
US 2020/0150003 A1     May 14, 2020

Related U.S. Application Data

(63) Continuation of application No. 16/231,762, filed on Dec. 24, 2018, now Pat. No. 10,545,074, which is a
(Continued)

(51) Int. Cl.
*B25J 9/16*           (2006.01)
*G01N 1/22*         (2006.01)
(Continued)

(52) U.S. Cl.
CPC .......... *G01N 1/2273* (2013.01); *B25J 9/163* (2013.01); *B25J 9/1656* (2013.01); *B25J 9/1694* (2013.01);
(Continued)

(58) Field of Classification Search
CPC . B25J 9/1664; B25J 9/16; B25J 9/1656; B25J 9/163; G05B 15/00; G05B 19/00; G05B 2219/40103
(Continued)

(56) References Cited

U.S. PATENT DOCUMENTS

| 4,687,457 A | 8/1987 | Milner |
| 4,820,233 A | 4/1989 | Weiner |

(Continued)

FOREIGN PATENT DOCUMENTS

| CN | 102226740 A | 10/2011 |
| JP | H0487423 A | 3/1992 |

(Continued)

OTHER PUBLICATIONS

Lin, I-Shen, et al., "An Advanced Telerobotic Control System for a Mobile Robot with Multisensor Feedback," 1995, ResearchGate, Proc. of Intelligent Autonomous Systems(IAS-4), Mar. 1995, 365-372. (Year: 1995).*

(Continued)

*Primary Examiner* — Jaime Figueroa
(74) *Attorney, Agent, or Firm* — Young Basile Hanlon & MacFarlane, P.C.

(57) ABSTRACT

A method includes receiving, from an imaging device associated with a robotic apparatus, an image signal including an object of interest represented in the image signal; receiving, by the robotic apparatus from an external agent, a task indication related to the object of interest, the task indication representative of a task to be performed by the robotic apparatus with respect to the object of interest; and responsive to receipt of the task indication: detecting salient features of the object of interest within the image; storing, by the robotic apparatus, a task context, the task context comprising data pertaining to the salient features and data pertaining to the task indication; and commencing, by the robotic apparatus, the task with respect to the object of interest.

20 Claims, 20 Drawing Sheets

Related U.S. Application Data continuation of application No. 15/852,821, filed on Dec. 22, 2017, now Pat. No. 10,213,921, which is a continuation of application No. 15/269,761, filed on Sep. 19, 2016, now Pat. No. 9,868,208, which is a continuation of application No. 14/625,464, filed on Feb. 18, 2015, now Pat. No. 9,446,515, which is a continuation of application No. 13/601,721, filed on Aug. 31, 2012, now Pat. No. 9,186,793.

(51) Int. Cl.
| | |
|---|---|
| *G05B 19/42* | (2006.01) |
| *B60K 11/02* | (2006.01) |
| *F01P 3/20* | (2006.01) |
| *G01N 1/44* | (2006.01) |
| *G01N 33/00* | (2006.01) |
| *F01P 7/16* | (2006.01) |
| *F01P 11/16* | (2006.01) |
| *G01N 30/72* | (2006.01) |
| *G01N 35/00* | (2006.01) |

(52) U.S. Cl.
CPC ............... *B60K 11/02* (2013.01); *F01P 3/20* (2013.01); *G01N 1/44* (2013.01); *G01N 33/0016* (2013.01); *G05B 19/42* (2013.01); *B60Y 2400/432* (2013.01); *B60Y 2400/433* (2013.01); *F01P 7/16* (2013.01); *F01P 11/16* (2013.01); *G01N 30/72* (2013.01); *G01N 33/0047* (2013.01); *G01N 2001/2288* (2013.01); *G01N 2035/00475* (2013.01); *G05B 2219/31048* (2013.01); *G05B 2219/36447* (2013.01); *G05B 2219/40103* (2013.01); *Y02P 90/02* (2015.11)

(58) Field of Classification Search
USPC .......................................... 700/245–264, 259
See application file for complete search history.

(56) References Cited

U.S. PATENT DOCUMENTS

| | | | |
|---|---|---|---|
| 4,853,771 A | 8/1989 | Witriol | |
| 4,889,027 A | 12/1989 | Yokoi | |
| 5,042,807 A | 8/1991 | Sasakawa | |
| 5,063,603 A | 11/1991 | Burt | |
| 5,355,435 A | 10/1994 | DeYong | |
| 5,369,497 A | 11/1994 | Allen | |
| 5,378,188 A | 1/1995 | Clark | |
| 5,638,359 A | 6/1997 | Peltola | |
| 5,652,594 A | 7/1997 | Costas | |
| 5,673,367 A | 9/1997 | Buckley | |
| 5,875,108 A | 2/1999 | Hoffberg | |
| 6,009,418 A | 12/1999 | Cooper | |
| 6,014,653 A | 1/2000 | Thaler | |
| 6,253,058 B1 | 6/2001 | Murasaki | |
| 6,259,988 B1 | 7/2001 | Galkowski | |
| 6,338,013 B1 | 1/2002 | Ruffner | |
| 6,429,291 B1 | 8/2002 | Turley | |
| 6,435,936 B1 | 8/2002 | Rehkemper | |
| 6,458,157 B1 | 10/2002 | Suaning | |
| 6,545,705 B1 | 4/2003 | Sigel | |
| 6,545,708 B1 | 4/2003 | Tamayama | |
| 6,546,291 B2 | 4/2003 | Merfeld | |
| 6,547,631 B1 | 4/2003 | Randall | |
| 6,560,511 B1 | 5/2003 | Yokoo | |
| 6,565,407 B1 | 5/2003 | Woolington | |
| 6,581,046 B1 | 6/2003 | Ahissar | |
| 6,600,418 B2 * | 7/2003 | Francis | G06Q 10/087 340/572.1 |
| 6,615,108 B1 | 9/2003 | Peless | |
| 6,682,392 B2 | 1/2004 | Chan | |
| 6,697,711 B2 | 2/2004 | Yokono | |
| 6,760,645 B2 | 7/2004 | Kaplan | |
| 6,774,908 B2 | 8/2004 | Bates | |
| 7,023,833 B1 | 4/2006 | Aiello | |
| 7,054,850 B2 | 5/2006 | Matsugu | |
| 7,235,013 B2 | 6/2007 | Kobayashi | |
| 7,418,320 B1 | 8/2008 | Bodin | |
| 7,565,203 B2 | 7/2009 | Greenberg | |
| 7,765,029 B2 | 7/2010 | Fleischer | |
| 7,849,030 B2 | 12/2010 | Ellingsworth | |
| 8,015,130 B2 | 9/2011 | Matsugu | |
| 8,015,785 B2 | 9/2011 | Walker | |
| 8,140,188 B2 * | 3/2012 | Takemitsu | B25J 9/1661 700/245 |
| 8,145,355 B2 | 3/2012 | Danko | |
| 8,145,492 B2 | 3/2012 | Fujita | |
| 8,154,436 B2 | 4/2012 | Szajnowski | |
| 8,281,997 B2 | 10/2012 | Moran | |
| 8,315,305 B2 | 11/2012 | Petre | |
| 8,346,692 B2 | 1/2013 | Rouat | |
| 8,386,079 B1 * | 2/2013 | Kohler | G06N 3/008 700/246 |
| 8,466,777 B2 * | 6/2013 | Matsumoto | G06Q 10/06 340/10.5 |
| 8,467,623 B2 | 6/2013 | Izhikevich | |
| 8,515,160 B1 | 8/2013 | Khosla | |
| 8,527,094 B2 | 9/2013 | Kumar | |
| 8,583,286 B2 | 11/2013 | Fleischer | |
| 8,712,939 B2 | 4/2014 | Szatmary | |
| 8,712,941 B2 | 4/2014 | Izhikevich | |
| 8,719,199 B2 | 5/2014 | Izhikevich | |
| 8,725,658 B2 | 5/2014 | Izhikevich | |
| 8,725,662 B2 | 5/2014 | Izhikevich | |
| 8,731,295 B2 | 5/2014 | Schepelmann | |
| 8,756,183 B1 | 6/2014 | Daily | |
| 8,775,341 B1 | 7/2014 | Commons | |
| 8,793,205 B1 | 7/2014 | Fisher | |
| 8,880,222 B2 * | 11/2014 | Kawamoto | B25J 9/1664 700/259 |
| 8,943,008 B2 | 1/2015 | Ponulak | |
| 8,954,193 B2 | 2/2015 | Sandin | |
| 8,972,315 B2 | 3/2015 | Szatmary | |
| 8,977,582 B2 | 3/2015 | Richert | |
| 8,983,216 B2 | 3/2015 | Izhikevich | |
| 8,990,133 B1 | 3/2015 | Ponulak | |
| 8,996,177 B2 | 3/2015 | Coenen | |
| 9,043,952 B2 | 6/2015 | Sandin | |
| 10,427,306 B1 * | 10/2019 | Quinlan | G06F 3/017 |
| 2001/0045809 A1 | 11/2001 | Mukai | |
| 2002/0038294 A1 | 3/2002 | Matsugu | |
| 2002/0072293 A1 | 6/2002 | Beyo | |
| 2002/0081937 A1 | 6/2002 | Yamada | |
| 2002/0156556 A1 | 10/2002 | Ruffner | |
| 2002/0158599 A1 | 10/2002 | Fujita | |
| 2002/0183895 A1 | 12/2002 | Kaplan | |
| 2002/0198854 A1 | 12/2002 | Berenji | |
| 2003/0050903 A1 | 3/2003 | Liaw | |
| 2003/0222987 A1 | 12/2003 | Karazuba | |
| 2003/0232568 A1 | 12/2003 | Engel | |
| 2004/0016638 A1 | 1/2004 | LaConti | |
| 2004/0153211 A1 | 8/2004 | Kamoto | |
| 2004/0158358 A1 | 8/2004 | Anezaki | |
| 2004/0162638 A1 | 8/2004 | Solomon | |
| 2004/0193670 A1 | 9/2004 | Langan | |
| 2004/0212148 A1 | 10/2004 | Losey | |
| 2004/0220082 A1 | 11/2004 | Surmeier | |
| 2005/0015351 A1 | 1/2005 | Nugent | |
| 2005/0022751 A1 | 2/2005 | Nelson | |
| 2005/0036649 A1 | 2/2005 | Yokono | |
| 2005/0049749 A1 | 3/2005 | Watanabe | |
| 2005/0065651 A1 | 3/2005 | Ayers | |
| 2005/0209749 A1 | 9/2005 | Ito | |
| 2005/0283450 A1 | 12/2005 | Matsugu | |
| 2006/0069448 A1 | 3/2006 | Yasui | |
| 2006/0161218 A1 | 7/2006 | Danilov | |
| 2006/0195226 A1 | 8/2006 | Matsukawa | |
| 2007/0037475 A1 | 2/2007 | Spear | |
| 2007/0061041 A1 * | 3/2007 | Zweig | G05D 1/0261 700/245 |
| 2007/0150106 A1 | 6/2007 | Hashimoto | |

(56) References Cited

U.S. PATENT DOCUMENTS

| | | |
|---|---|---|
| 2007/0176643 A1 | 8/2007 | Nugent |
| 2007/0208678 A1 | 9/2007 | Matsugu |
| 2007/0239315 A1 | 10/2007 | Sato |
| 2007/0258329 A1 | 11/2007 | Winey |
| 2008/0039974 A1 | 2/2008 | Sandin |
| 2008/0201282 A1 | 8/2008 | Garcia |
| 2008/0294074 A1 | 11/2008 | Tong |
| 2009/0014402 A1 | 1/2009 | Wolf |
| 2009/0043722 A1 | 2/2009 | Nugent |
| 2009/0146795 A1* | 6/2009 | Matsumoto .......... G06Q 10/087 340/10.5 |
| 2009/0153499 A1 | 6/2009 | Kim |
| 2009/0287624 A1 | 11/2009 | Rouat |
| 2010/0086171 A1 | 4/2010 | Lapstun |
| 2010/0091286 A1 | 4/2010 | Dahlgren |
| 2010/0166320 A1 | 7/2010 | Paquier |
| 2010/0250022 A1 | 9/2010 | Hines |
| 2010/0283853 A1 | 11/2010 | Acree |
| 2010/0286824 A1 | 11/2010 | Solomon |
| 2010/0292835 A1 | 11/2010 | Sugiura |
| 2011/0016071 A1 | 1/2011 | Guillen |
| 2011/0071675 A1* | 3/2011 | Wells ..................... H04N 5/332 700/250 |
| 2011/0119214 A1 | 5/2011 | Breitwisch |
| 2011/0119215 A1 | 5/2011 | Elmegreen |
| 2011/0178658 A1 | 7/2011 | Kotaba |
| 2011/0184556 A1 | 7/2011 | Seth |
| 2011/0228742 A1 | 9/2011 | Honkasalo |
| 2011/0235698 A1 | 9/2011 | Petre |
| 2011/0245974 A1* | 10/2011 | Kawamoto ............ B25J 9/1664 700/259 |
| 2012/0011090 A1 | 1/2012 | Tang |
| 2012/0098933 A1 | 4/2012 | Robinson |
| 2012/0109866 A1 | 5/2012 | Modha |
| 2012/0117012 A1 | 5/2012 | Szatmary |
| 2012/0143495 A1 | 6/2012 | Dantu |
| 2012/0173021 A1 | 7/2012 | Tsusaka |
| 2012/0185092 A1 | 7/2012 | Ku |
| 2012/0209428 A1 | 8/2012 | Mizutani |
| 2012/0209432 A1 | 8/2012 | Fleischer |
| 2012/0211923 A1 | 8/2012 | Garner |
| 2012/0303091 A1 | 11/2012 | Izhikevich |
| 2012/0308076 A1 | 12/2012 | Piekniewski |
| 2012/0308136 A1 | 12/2012 | Izhikevich |
| 2012/0330872 A1 | 12/2012 | Esser |
| 2013/0030570 A1 | 1/2013 | Shimizu |
| 2013/0046716 A1 | 2/2013 | Chan |
| 2013/0073491 A1 | 3/2013 | Izhikevich |
| 2013/0073496 A1 | 3/2013 | Szatmary |
| 2013/0073500 A1 | 3/2013 | Szatmary |
| 2013/0077597 A1 | 3/2013 | Nukala |
| 2013/0103626 A1 | 4/2013 | Hunzinger |
| 2013/0116827 A1 | 5/2013 | Inazumi |
| 2013/0117212 A1 | 5/2013 | Hunzinger |
| 2013/0151450 A1 | 6/2013 | Ponulak |
| 2013/0176423 A1 | 7/2013 | Rischmuller |
| 2013/0204814 A1 | 8/2013 | Hunzinger |
| 2013/0204820 A1 | 8/2013 | Hunzinger |
| 2013/0216144 A1 | 8/2013 | Robinson |
| 2013/0218821 A1 | 8/2013 | Szatmary |
| 2013/0251278 A1 | 9/2013 | Izhikevich |
| 2013/0314502 A1 | 11/2013 | Urbach |
| 2013/0325768 A1 | 12/2013 | Sinyavskiy |
| 2013/0325773 A1 | 12/2013 | Sinyavskiy |
| 2013/0325774 A1 | 12/2013 | Sinyavskiy |
| 2013/0325775 A1 | 12/2013 | Sinyavskiy |
| 2013/0345872 A1 | 12/2013 | Brooks |
| 2014/0008496 A1 | 1/2014 | Ye |
| 2014/0016858 A1 | 1/2014 | Richert |
| 2014/0032021 A1 | 1/2014 | Metzler |
| 2014/0089232 A1 | 3/2014 | Buibas |
| 2014/0175267 A1 | 6/2014 | Thiel |
| 2014/0276951 A1 | 9/2014 | Hourtash |
| 2015/0073596 A1 | 3/2015 | Fudaba |
| 2015/0234385 A1 | 8/2015 | Sandin |
| 2015/0378444 A1* | 12/2015 | Yin .......................... G06K 9/52 345/156 |
| 2016/0179096 A1 | 6/2016 | Bradlow |

FOREIGN PATENT DOCUMENTS

| | | |
|---|---|---|
| RU | 2108612 C1 | 4/1998 |
| WO | 2008083335 A2 | 7/2008 |
| WO | 2010136961 A1 | 12/2010 |

OTHER PUBLICATIONS

Ishii, K, Designing laser gesture interface for robot control, 2009, . In Human-Computer Interaction—INTERACT 2009—12th IFIP TC 13 International Conference, Proceedings (Part 2 ed., pp. 479-492. (Year: 2009).*

C. C. Kemp, C. D. Anderson, H. Nguyen, A. J. Trevor and Z. Xu, "A point-and-click interface for the real world: Laser designation of objects for mobile manipulation," 2008 3rd ACM/IEEE International Conference on Human-Robot Interaction (HRI), 2008, pp. 241-248, doi: 10.1145/1349822.1349854. (Year: 2008).*

Asensio et al., 'Robot Learning Control Based on Neural Network Prediction' ASME 8th Annual Dynamic Systems and Control Conference joint with the JSME 11th Motion and Vibration Conference 2012 [Retrieved on: Jun. 24, 2014]. Retrieved fro internet: <http://msc.berkeley.edu/wjchen/publications/DSC12_8726._FI.pdf>. 11 pages.

Baluja, S., et al., 'Expectation-based Selective Attention for Visual Monitoring and Control of a Robot Vehicle,' Robotics and Autonomous Systems, 1997, pp. 329-344.

Bill Steele, The Human Touch Makes Robots Defter, Nov. 6, 2013, Cornell Chronicle. http://www.news.cornell.edu/stories/2013/11/human-touch-makes-robots-defter. 2 pages.

Bohte, 'Spiking Nueral Networks' Doctorate at the University of Leiden, Holland, Mar. 5, 2003, pp. 1-133 [retrieved on Nov. 14, 2012]. Retrieved from the internet: <URL: http://homepages.cwi.nl/-sbohte/publication/phdthesis.pdf>. 148 pages.

Bouganis et al., Training a Spiking Neural Network to Control a 4-DoF Robotic Arm based on Spiking Timing-Dependent Plasticity in WCCI 2010 IEEE World Congress on Computational Intelligence Jul. 2010 [Retrieved on Jun. 24, 2014] Retrieved from internet: <http://www.doc.ic.ac.uk/-mpsha/IJCNN10a.pdf. 8 pages.

Brette et al., Brian: a simple and flexible simulator for spiking neural networks, The Neuromorphic Engineer, Jul. 1, 2009, pp. 1-4, doi: 10.2417/1200906.1659.

Brette, et al., "Simulation of Networks of Spiking Neurons: A Review of Tools and Strategies", Received Nov. 29, 2006, Revised Apr. 2, 2007, Accepted Apr. 12, 2007, Springer Science, 50 pages.

Bush, Daniel, "STDP, Rate-coded Hebbian Learning and Auto-Associative Network Models of the Hippocampus", Sep. 2008, University of Sussex, pp. 1-109.

Chistiakova, Marina, and Maxim Volgushev. "Heterosynaptic plasticity in the neocortex." Experimental brain research 199.3-4 (2009): 377-390.

Competitive behaviors of a spiking neural network with spike timing dependent plasticity, Chengmei Ruan ; Qingxiang Wu ; Lijuan Fan ; Zhiciiang Zhuo ; Xiaowei Wang, Biomedical Engineering and Informatics (BMEI), 2012 5th International Conference on DOI: 10.1109/BMEI.2012.6513088 Publication Year: 2012 , pp. 1015-1019.

Coupard, Pierre-Philippe, An Availabot-like computer-controlled push puppet for Linux, https://web.archive.org/web/20081106161941/http://myspace.voo.be/pcoupard/push_p uppet_to_y/, 2008. 7 pages.

Cuntz et al., 'One Rule to Grow Them All: A General Theory of Neuronal Branching and Its Paractical Application' PLOS Computational Biology, 6 (8), Published Aug. 5, 2010, pp. 1-14.

Davison et al., PyNN: a common interface for neuronal network simulators, Frontiers in Neuroinformatics, Jan. 2009, pp. 1-10, vol. 2, Article 11.

Djurfeldt, Mikael, The Connection-set Algebra: a formalism for the representation of connectivity structure in neuronal network mod-

(56) References Cited

OTHER PUBLICATIONS els, implementations in Python and C++, and their use in simulators BMC Neuroscience Jul. 18, 2011 p. 1 12(Suppl 1):P80.

Fidjeland et al., Accelerated Simulation of Spiking Neural Networks Using GPUs [online], 2010 [retrieved on Jun. 15, 2013], Retrieved from the Internet: URL:http://ieexplore.iece.org/xpls/abs_all.jsp?arnmber=55-96678&tag=1. 8 pages.

Fidjeland, et al., 'Accelerated Simulation of Spiking Neural Networks Using GPUs,' WCCI 2010 IEEE World Congress on Computational Intelligience, Jul. 18-23, 2010—CCIB, Barcelona, Spain, pp. 536-543, [retrieved on Nov. 14, 2012]. Retrieved from the Internet: URL:http://www.doc.ic.ac.ukl-mpsha/IJCNN10b.pdf.

Fletcher, L., et al., "Correlating Driver Gaze with the Road Scene for Driver Assistance Systems," Robotics and Autonomous Systems, 2005, pp. 71-84.

Floreano et al., 'Neuroevolution: from architectures to learning' Evol. Intel. Jan. 1, 2008: pp. 47-62, [retrieved Dec. 30, 2013] [retrieved online from URL:<http://inforscience.epfl.ch/record/112676/files/FloreanoDuerrMattiussi2008. pdf>.

Gewaltig et al., 'NEST (Neural Simulation Tool)', Scholarpedia, 2007, pp. 1-15, 2(4): 1430, doi: 1 0.4249/scholarpedia.1430.

Glackin, C. et al., Feature Extraction from Spectra-temporal Signals using Dynamic Synapses, recurrency, and lateral inhibition, Neural Networks (IJCNN), The 2010 International Joint Conference on DOI: 10.1109/IJCNN.2010.5596818 Publication Year: 2010, pp. 1-6.

Gleeson et al., NeuroML: A Language for Describing Data Driven Models of Neurons and Networks with a High Degree of Biological Detail, PLoS Computational Biology, Jun. 2010, pp. 1-19 vol. 6 Issue 6.

Goodman et al, Brian: a simulator for spiking neural networks in Python, Frontiers in Neuroinformatics, Nov. 2008, pp. 1-10, vol. 2, Article 5.

Gorchetchnikov et al., NineML: declarative, mathematically-explicit descriptions of spiking neuronal networks, Frontiers in Neuroinformatics, Conference Abstract: 4th INCF Congress of Neuroinformatics, doi: 1 0.3389/conf.fninf.2011.08.00098, 2 pgs.

Graham, Lyle J., The Surf-Hippo Reference Manual, http://www.neurophys.biomedical.univparisS.fr/-graham/surf-hippo-files/Surf-Hippo% 20Reference%2QManual.pdf, Mar. 2002, pp. 1-128.

Hardware and Software Platform for Mobile Manipulation R&D, 2012, https://web.archive.org/web/20120128031010/http://www.willowgarage.com/pages/pr2 /design. 4 pages.

Huh et al., 'Real-Time Motor Control Using Recurrent Neural Networks' IEEEE Apr. 2009, 7 pages.

Huh et al., 'Generalized Power Law for Curve Movements' 2011, pp. 1-2.

Huh, 'Rethinking Optimal Control of Human Movements' Thesis 2012, 115 pages.

Ishii K., et al., Designing Laser Gesture Interface for Robot Control, Springer Berlin Heidelberg, Proceedings, Part II 12th IFIP TC 13 International Conference, Uppsala, Sweden, Aug. 24-28, 2009, Proceedings, pp. 479-492.

Itti, Laurent, and Christof Koch. 'Computational modelling of visual attention.'Nature reviews neuroscience 2.3 (2001): 194-203.

Izhikevich E.M., 'Neural Excitability, Spiking and Bursting', Neurosciences Institute, Received Jun. 9, 1999, Revised Oct. 25, 1999, 1171-1266, 96 pages.

Izhikevich et al., 'Relating STDP to BCM', Neural Computation (2003) 15, pp. 1511-1523.

Izhikevich, 'Polychronization: Computation with Spikes', Neural Computation, 25, 2006, 18, 245-282.

Izhikevich, 'Simple Model of Spiking Neurons'IEEE Transactions on Neural Networks, vol. 14, No. 6, Nov. 2003, pp. 1569-1572.

Izhikevich, Eugene M., Dynamical systems in neuroscience: chapters 1 and 2, MIT press, 2007. 67 pages.

Jain, Learning Trajectory Preferences for Manipulators via Iterative Improvement, 2013, Advances in Neural Information Processing Systems 26 (NIPS 2013). 8 pages.

Judd, T., et al., "Learning to Predict where Humans look," 12th International Conference on Computer Vision, 2009, 8 pages.

Karbowski et al., 'Multispikes and Synchronization in a Large Neural Network with Temporal Delays', Neural Computation 12; (2000), pp. 1573-1606.

Kasabov, 'Evolving Spiking Neural Networks for Spatio-and Spectro-Temporal Pattern Recognition', IEEE 6th International Conference 'Intelligent Systems' 2012 [Retrieved on Jun. 24, 2014], Retrieved from internet: <http:// ncs.ethz.ch/projects/evospike/publications/evolving-spiking-neural-networks-for- spatio-and-spectro-temporal-pattem-recognition-plenary-talk-ieee-is> 6 pages.

Kazantsev, et al., 'Active Spike Transmission in the Neuron Model With a Winding Threshold Maniford', Jan. 3, 2012,205-211,7 pages.

Khotanzad, 'Classification of invariant image representations using a neural network' IEEF. Transactions on Acoustics, Speech, and Signal Processing, vol. 38, No. 6, Jun. 1990, pp. 1028-1038 [online], [retrieved on Dec. 10, 2013]. Retrieved from the Internet <URL: http://www-ee.uta.edu/eeweb/IP/Courses/SPR/Reference/Khotanzad.pdf>.

Kling-Petersen, PhD, "Sun and HPC: From Systems to PetaScale" Sun Microsystems, no date, 31 pages.

Knoblauch A., et al., 'Memory Capacities for Synaptic and Structural Plasticity,' Neural Computation, 2010, vol. 22 (2), pp. 289-341.

Laurent, 'The Neural Network Query Language (NNQL) Reference' [retrieved on Nov. 12, 2013]. 1 pg., Retrieved from the Internet: <URL https://code.google.com/p/nnql/issues/detail?id=1>.

Leydesdorff L., et al., 'Classification and Powerlaws: The Logarithmic Transformation, Journal of the American Society for Information Science and Technology (forthcoming)', 2006. 1 page.

Li, Zhaoping. "A saliency map in primary visual cortex." Trends in cognitive sciences 6.1 (2002): 9-16.

Markram, Henry, et al. "Regulation of synaptic efficacy by coincidence of postsynaptic APs and EPSPs." Science 275.5297 (1997): 213-215.

Martinez-Perez, et al., "Automatic Activity Estimation Based on Object Behavior Signature", 2010, 10 pages.

Matsugu, et al., "Convolutional Spiking Neural Network for Robust Object Detection with Population Code Using Structured Pulse Packets", 2004, 39-55, 17 pages.

Medini. C., et al., Modeling Cerebellar Granular layer Excitability and Combinatorial Computation with Spikes, Bio-Inspired Computing: Theories and Applications (BIC-TA), 2010 IEEE Fifth International Conference on DOI: 10.1 109/BICTA.201 0.5645274, Publication Year: 2010, pp. 1495-1503.

Meinhardt, Hans, and Alfred Gierer. 'Pattern formation by local self-activation and lateral inhibition.' Bioessays 22.8 (2000): 753-760.

Mordatch et al, 'Discovery of Complex Behaviors through Contract-Invariant Optimization' ACM Transactions on Graphics (TOG)—SIGGRAPH 2012 Conference, 8 pages.

Munn, S., et al., "Fixation-identification in Dynamic Scenes: Comparing an Automated Algorithm to Manual Coding," Proceedings of the 5th symposium on Applied Perception in Graphics and Visualization, 2008, pp. 33-42.

Nichols, A Re configurable Computing Architecture for Implementing Artificial Neural Networks on FPGA, Master's Thesis, The University of Guelph, 2003, pp. 1-235.

Niv, et al., Evolution of Reinforcement Learning in Uncertain Environments: A Simple Explanation for Complex Foraging Behaviors, International Society for Adaptive Behavior, 2002, vol. 10(1), pp. 5-24.

Ostojic, Srdjan, Nicolas Brunel, From Spiking Neuron Models to Linear-Nonlinear Models, Jan. 2011, vol. 7 (1), e1001056. 1 page.

Paugam-Moisy et al., 'Computing with spiking neuron networks' G. Rozenberg T. Back, J. Kok (Eds.), Handbook of Natural Computing, Springer-Verlag (2010) [retrieved Dec. 30, 2013], [retrieved online from link.springer.com], 5 pgs.

Pavlidis et al. Spiking neural network training using evolutionary algorithms. In: Proceedings 2005 IEEE International Joint Conference on Neural Nelworkds, 2005. UCNN'05, vol. 4, pp. 2190-2194 Publication Date Jul. 31, 2005 [online] [Retrieved on Dec. 10, 2013]

(56) References Cited

OTHER PUBLICATIONS

Retrieved from the Internet <URL: http://citeseerx.ist.psu.edu/ viewdoe/down!oad?doi=10.1.1.5.4346&rep=:rep1&type=pdf.

PCT International Search Report for PCT/US2014/026685 dated Oct. 3, 2014. 4 pages.

PCT International Search Report for PCT/US2014/026738 dated Jul. 21, 2014. 2 pages.

Pham et al, 'Affine invariance of human hand movements: a direct test' 2012, 23 pages.

PR2 User Manual, Oct. 5, 2012. 40 pages.

QingXiang Wu et al, Edge Detection Based on Spiking Neural Network Model, ICIC 2007, LNAI 4682, pp. 26-34,2007, Springer-Verlag, Berlin Heidelberg.

Ramachandran, et al., 'The Perception of Phantom Limbs', The D.O. Hebb Lecture, Center for Brain and Cognition, University of California, 1998, 121, 1603-1630,28 pages.

Schaal et al., An Example Application of Policy Improvement with Path Integrals (PI.sup.2), Jun. 9, 2010. 6 pages.

Schemmel, J., et al., Implementing Synaptic Plasticity in a VLSI Spiking Neural Network Model. In: Proceedings of the 2006 International Joint Conference on Neural Networks (IJCNN'06), IEEE Press (2006) Jul. 16-21, 2006, pp. 1-6 [online], [retrieved on Aug. 24, 2012]. Retrieved from the Internet <URL: http://www.kip.uniheidelberg. deNeroeffentlichungen/download.cgi/4620/ps/1774.pdf> Introduction.

Simulink.RTM. model [online], [Retrieved on Dec. 10, 2013] Retrieved from URL: http://www.mathworks.com/ products/simulink/index.html> (2 pgs).

Sinyavskiy et al. 'Reinforcement learning of a spiking neural network in the task of control of an agent in a virtual discrete environment' Rus, J. Nonlin. Dyn., 2011, vol. 7, No. 4 (Mobile Robots), pp. 859-875, chapters 1-8 (Russian Article with English Abstract).

Sjostrom et al., 'Spike-Timing Dependent Plasticity' Scholarpedia, 5(2):1362 (2010), pp. 1-18.

Stringer, et al., "Invariant Object Recognition in the Visual System with Novel Views of 3D Objects", 2002, 2585-2596, 12 pages.

Suzuki et al.,Operation Direction to a Mobile Robot by Projection Lights, 2005 IEEE Workshop on Advanced Robotics and its Social Impacts, Jun. 12-15, 2005, pp. 160-165.

Swat: A Spiking Neural Network Training Algorithm for Classification Problems, Wade, J.J. ; McDaid, L.J. ; Santos, J.A. ; Sayers, H.M., Neural Networks, IEEE Transactions on vol. 21 , Issue: 11 DOI: 10.1109/TNN.2010.2074212 Publication Year: 2010 , pp. 1817-1830.

Swiercz, Waldemar, et al. 'A new synaptic plasticity rule for networks of spiking neurons.' Neural Networks, IEEE Transactions on 17.1 (2006): 94-105.

Szatmary et al., 'Spike-timing Theory of Working Memory' PLoS Computational Biology, vol. 6, Issue 8, Aug. 19, 2010 [retrieved on Dec. 30, 2013]. Retrieved from the Internet: <URL: http://www.ploscompbiol.org/article/info%3Adoi%2F10.1371%2Fjournal.pcbi.10008 79#> (11 pgs).

Tank D.W., et al., 'Neural Computation by Concentrating Information in Time,' Proceedings of the National Academy of Sciences of the United States of America, 1987, vol. 84 (7), pp. 1896-1900.

Thorpe, S.J., Delorme, A. & VanRullen, R. (2001). Spike-based strategies for rapid processing. Neural Networks 14, pp. 715-725.

Thorpe, S.J., Guyonneau, R., Guilbaud, N Allegraud, J-M, & VanRullen, R. (2004), SpikeNet: real-time visual processing with one spike per neuron. Neurocomputing, 58-60, pp. 857-864.

Todorov 'Direct Cortical Control of Muscle activation in voluntary arm movements: a model' Nature America Inc. http://neurosci.nature.com 2000, 8 pages.

Victor, T., et al., "Sensitivity of Eye-movement Measurements to in-vehicle Task Difficulty," Transportation Research Part F: Traffic Psychology and Behavior, 2005, pp. 167-190.

Voutsas, K. ; Adamy, .J., A Biologically Inspired Spiking Neural Network for Sound Source Lateralization Neural Networks, IEEE Transactions on vol. 18, Issue: 6 DOI: 10.11 09/TNN.2007.899623, Publication Year: 2007, pp. 1785-1799.

Wennekers, T., Analysis of Spatia-temporal Patterns in Associative Networks of Spiking Neurons Artificial Neural Networks, 1999. 1CANN 99. Ninth International Conference on (Conf. Publ. No. 470) vol. 1 D01:10.1049/cp:19991116 Publication Year: 1999, vol. 1, pp. 245-250.

Won, W.J., et al., 'Implementation of Road Traffic Signs Detection based on Saliency Map Model,' IEEE Intelligent Vehicles Symposium, 2008, pp. 542-547.

Wu, QingXiang, et al. 'Remembering Key Features of Visual Images based on Spike Timing Dependent Plasticity of Spiking Neurons.' Image and Signal Processing, 2009. CISP'09. 2nd International Congress on. IEEE, 2009. 5 pages.

* cited by examiner

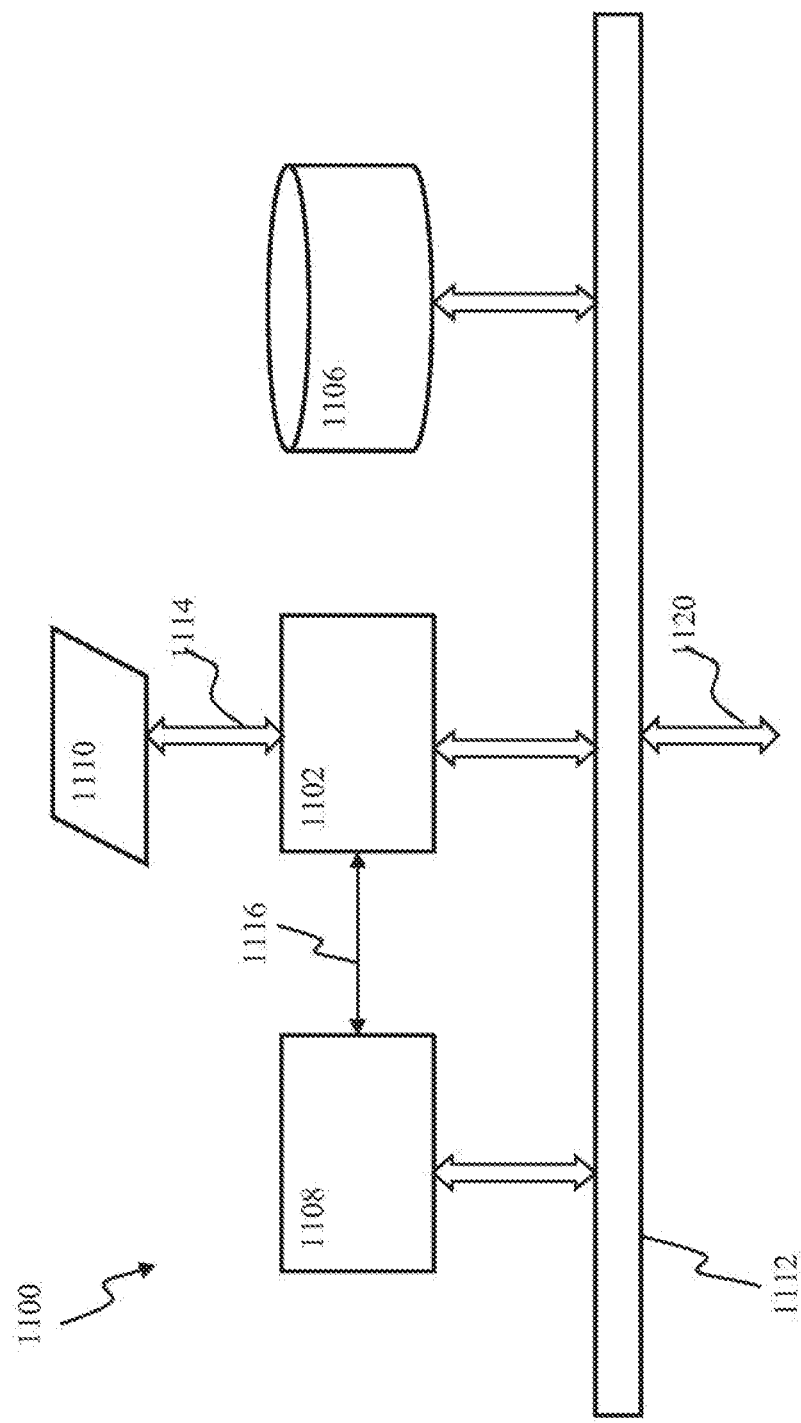

APPARATUS AND METHODS FOR CONTROLLING ATTENTION OF A ROBOT

CROSS-REFERENCE TO RELATED APPLICATIONS

This application is a continuation of entitled co-owned patent application Ser. No. 16/231,762, "APPARATUS AND METHODS FOR CONTROLLING ATTENTION OF A ROBOT, filed Dec. 24, 2018, which is a continuation of co-owned U.S. patent application Ser. No. 15/852,821, entitled "APPARATUS AND METHODS FOR CONTROLLING ATTENTION OF A ROBOT, filed Dec. 22, 2017, now U.S. Pat. No. 10,213,921, which is a continuation of co-owned U.S. patent application Ser. No. 15/269,761, entitled "APPARATUS AND METHOD FOR CONTROLLING ATTENTION OF A ROBOT," filed Sep. 19, 2016, now U.S. Pat. No. 9,868,208, which is a continuation of co-owned U.S. patent application Ser. No. 14/625,464, entitled "APPARATUS AND METHOD FOR CONTROLLING ATTENTION OF A ROBOT," filed Feb. 18, 2015, now U.S. Pat. No. 9,446,515, which is a continuation of co-owned U.S. patent application Ser. No. 13/601,721 entitled "APPARATUS AND METHOD FOR CONTROLLING ATTENTION OF A ROBOT," filed on Aug. 31, 2012, now U.S. Pat. No. 9,186,793, each of the foregoing incorporated herein by reference in its entirety. This application is related to U.S. patent application Ser. No. 13/830,398 entitled "NEURAL NETWORK LEARNING AND COLLABORATION APPARATUS AND METHODS," filed on Mar. 14, 2013, now U.S. Pat. No. 9,208,432, U.S. patent application Ser. No. 13/487,576 entitled "DYNAMICALLY RECONFIGURABLE STOCHASTIC LEARNING APPARATUS AND METHODS," filed Jun. 4, 2012, now U.S. Pat. No. 9,015,092, and U.S. patent application Ser. No. 13/548,071, entitled "SPIKING NEURON NETWORK SENSORY PROCESSING APPARATUS AND METHODS," filed Jul. 12, 2012, now U.S. Pat. No. 8,977,582, the entire disclosures of which are hereby incorporated by reference.

COPYRIGHT

A portion of the disclosure of this patent document contains material that is subject to copyright protection. The copyright owner has no objection to the facsimile reproduction by anyone of the patent document or the patent disclosure, as it appears in the Patent and Trademark Office patent files or records, but otherwise reserves all copyright rights whatsoever.

BACKGROUND

The present disclosure relates to apparatus and methods for an external agent to control the attention of a robot.

Controlling attention of autonomous robotic systems may be often required in a wide variety of applications, such as exploration, search and rescue, inspection, and/or navigation. Approaches for controlling attention that rely on a pre-programmed attention factors may not always perform adequately, particularly when operating in a dynamically changing real-world environment full of distractors. Manipulation of robots attention is commonly performed by modifying the robots software state via remote commands. However, such approaches are not often desirable because 1) it is idiosyncratic to the internal representational system of the robot, not always intuitive to the user. Finally, deploying a large number of remote operators may be considered a problem.

SUMMARY

The present invention satisfies the foregoing needs by providing, inter alia, apparatus and methods for guiding the attention of robotic devices.

One aspect of the disclosure relates to a method for providing contextual instruction to a robotic apparatus. A signal may be transmitted using a carrier of first variety. The signal may be configured to irradiate an object. An indication may be transmitted using a carrier of second variety to the robotic apparatus. The second variety may be distinct from the first variety. The indication may convey whether detection of the first variety carrier is to be performed. The signal and the indication may provide the contextual instruction. The contextual instruction may be configured to cause the robotic apparatus to commence a task associated with the context.

In some implementations, the indication may be configured to inform the robotic apparatus of the signal transmission.

In some implementations, the carrier of the first variety may include one or more of a visible spectrum wave, an infrared spectrum wave, or an ultrasound wave. The carrier of the second variety may include one or both of an audible sound wave or an electromagnetic wave.

In some implementations, the carrier of the first variety may include one or both of (i) a visible spectrum carrier having a bandwidth associated therewith or (ii) a radio spectrum carrier having a multiple access sub-channel associated therewith. The bandwidth may be different from another bandwidth associated with another signal comprising the carrier of the first variety. The other signal and another indication may provide another context capable of causing another robotic apparatus to perform another task associated with the other context. The indication may be capable of being provided to the other robotic apparatus.

In some implementations, the task and the other task may be each configured to accomplish an outcome.

In some implementations, the carrier of the first variety may be undetectable by a human.

In some implementations, the task may be configured to accomplish a different outcome compared to another outcome accomplished by the other task.

In some implementations, the multiple access sub-channel may be configured to be distinct from another multiple access sub-channel associated with the other indication.

In some implementations, the carrier of the first variety may be characterized by a bandwidth. The bandwidth may be configured to overlap another bandwidth associated with another signal comprising the carrier of the first variety. The other signal and another indication may be capable of providing the context to another robotic apparatus to cause the other robotic apparatus to commence the task.

In some implementations, the overlap may be based on a design criterion associated with the carrier of the first variety. The design criterion may be configured to enable the robotic apparatus and the other robotic apparatus to engage in a competition for accomplishing the task.

In some implementations, a confirmation associated with the commencing of the task may be received from the robotic apparatus.

Another aspect of the disclosure relates to a remote interface apparatus for a robot operable in an environment.

The apparatus may comprise a transmitter, a tagging block, and a receiver. The transmitter may be capable of projecting a beam. The beam may be configured to form a footprint on at least a portion of the environment. The tagging block may be configured to send a tag associated with the portion to the environment. The receiver may be capable of receiving an indication from the robot, the indication being based on a receipt of the tag. One or more of the tag, the footprint, or an internal state of the robot may provide a robotic context. The context may be configured to cause the robot to perform a task associated with the context.

In some implementations, the beam may comprise a laser beam having a width that is smaller than a dimension of the footprint. The footprint may be characterized by a perimeter. The transmitter may be configured to trace the perimeter with the beam.

In some implementations, the beam may comprise a light beam having a beam width and a frequency associated therewith. The interface apparatus may be configured to facilitate beam adjustment to modify at least one of the beam width and the frequency.

In some implementations, the indication may be associated with the at least one robot. The indication may be further based on the at least one robot detecting at least a portion of the footprint.

Still another aspect of the disclosure relates to a method for use with an autonomous robotic inspection apparatus. A signal may be projected onto an object to be inspected. The projected signal may form a footprint on at least a portion of the object. The robot may be caused to detect the footprint. The robot may be caused to commence inspection of the portion of the object responsive to detecting the footprint.

In some implementations, the signal may comprise a waveform of a first variety. The inspection may comprise detection of waveforms of a second variety.

In some implementations, the waveform of the first variety may comprise an electromagnetic waveform. The waveforms of the second variety may comprise a pressure wave.

In some implementations, the waveform of the first variety may comprise a visible light waveform. The waveforms of the second variety may comprise an ultrasonic wave.

In some implementations, an indication may be transmitted to the robot inspection apparatus using a carrier of a variety that is different from the first variety. Commencing the inspection may be triggered based on the indication.

In some implementations, a confirmation may be provided by the robot inspection apparatus. The confirmation may be associated with commencing the inspection. The detection may be configured based on the indication.

In some implementations, the indication and the signal may form a context of a plurality of contexts. The context may be associated with the portion of the object. The robotic inspection apparatus may be configured to store the plurality of contexts to enable the robotic inspection apparatus to commence the inspection upon encountering the portion of the object. The encountering may be subsequent to the storing.

In some implementations, the detection may be configured independent of the indication.

Further features of the present invention, its nature and various advantages, will be more apparent from the accompanying drawings and the following detailed description.

BRIEF DESCRIPTION OF THE DRAWINGS

FIG. 11A is a block diagram illustrating a computerized system useful with the attention mapping methodology of the disclosure, according to some implementations.

Figure 1:
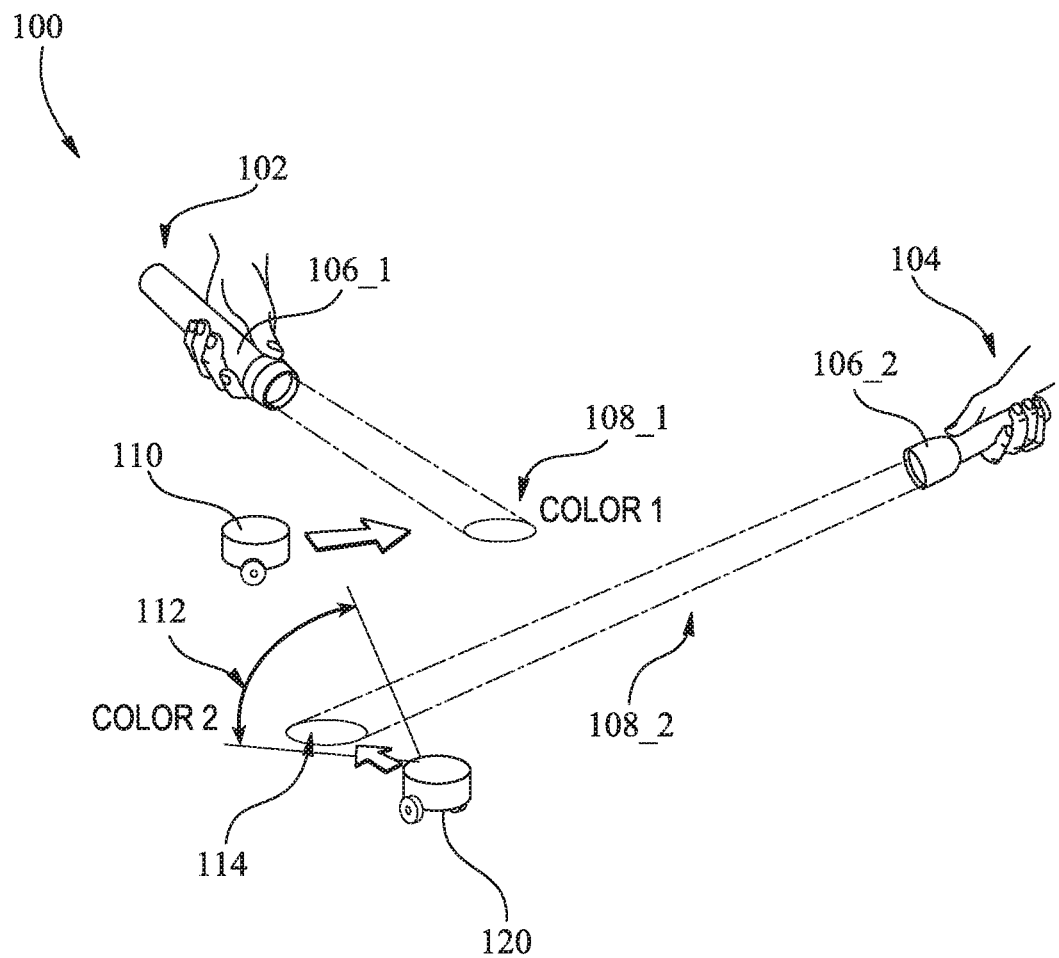
FIG. 1 is an illustration depicting a robot racing game comprising an attention spot light, according to some implementations.

All Figures disclosed herein are © Copyright 2015 Brain Corporation. All rights reserved.

DETAILED DESCRIPTION

Implementations of the present technology will now be described in detail with reference to the drawings, which are provided as illustrative examples so as to enable those skilled in the art to practice the technology. Notably, the figures and examples below are not meant to limit the scope of the present disclosure to a single implementation or implementation, but other implementations and implementations are possible by way of interchange of or combination with some or all of the described or illustrated elements. Wherever convenient, the same reference numbers will be used throughout the drawings to refer to same or like parts.

Where certain elements of these implementations can be partially or fully implemented using known components, only those portions of such known components that are necessary for an understanding of the present invention will be described, and detailed descriptions of other portions of such known components will be omitted so as not to obscure the disclosure.

In the present specification, an implementation showing a singular component should not be considered limiting; rather, the invention is intended to encompass other implementations including a plurality of the same component, and vice-versa, unless explicitly stated otherwise herein.

Further, the present disclosure encompasses present and future known equivalents to the components referred to herein by way of illustration.

As used herein, the term "bus" is meant generally to denote all types of interconnection or communication architecture that is used to access the synaptic and neuron memory. The "bus" may be optical, wireless, infrared, and/or another type of communication medium. The exact topology of the bus could be for example standard "bus", hierarchical bus, network-on-chip, address-event-representation (AER) connection, and/or other type of communication topology used for accessing, e.g., different memories in pulse-based system.

As used herein, the terms "computer", "computing device", and "computerized device "may include one or more of personal computers (PCs) and/or minicomputers (e.g., desktop, laptop, and/or other PCs), mainframe computers, workstations, servers, personal digital assistants (PDAs), handheld computers, embedded computers, programmable logic devices, personal communicators, tablet computers, portable navigation aids, J2ME equipped devices, cellular telephones, smart phones, personal integrated communication and/or entertainment devices, and/or any other device capable of executing a set of instructions and processing an incoming data signal.

As used herein, the term "computer program" or "software" may include any sequence of human and/or machine cognizable steps which perform a function. Such program may be rendered in a programming language and/or environment including one or more of C/C++, C #, Fortran, COBOL, MATLAB™, PASCAL, Python, assembly language, markup languages (e.g., HTML, SGML, XML, VoXML), object-oriented environments (e.g., Common Object Request Broker Architecture (CORBA)), Java™ (e.g., J2ME, Java Beans), Binary Runtime Environment (e.g., BREW), and/or other programming languages and/or environments.

As used herein, the terms "connection", "link", "transmission channel", "delay line", "wireless" may include a causal link between any two or more entities (whether physical or logical/virtual), which may enable information exchange between the entities.

As used herein, the term "memory" may include an integrated circuit and/or other storage device adapted for storing digital data. By way of non-limiting example, memory may include one or more of ROM, PROM, EEPROM, DRAM, Mobile DRAM, SDRAM, DDR/2 SDRAM, EDO/FPMS, RLDRAM, SRAM, "flash" memory (e.g., NAND/NOR), memristor memory, PSRAM, and/or other types of memory.

As used herein, the terms "integrated circuit", "chip", and "IC" are meant to refer to an electronic circuit manufactured by the patterned diffusion of trace elements into the surface of a thin substrate of semiconductor material. By way of non-limiting example, integrated circuits may include field programmable gate arrays (e.g., FPGAs), a programmable logic device (PLD), reconfigurable computer fabrics (RCFs), application-specific integrated circuits (ASICs), and/or other types of integrated circuits.

As used herein, the terms "microprocessor" and "digital processor" are meant generally to include digital processing devices. By way of non-limiting example, digital processing devices may include one or more of digital signal processors (DSPs), reduced instruction set computers (RISC), general-purpose (CISC) processors, microprocessors, gate arrays (e.g., field programmable gate arrays (FPGAs)), PLDs, reconfigurable computer fabrics (RCFs), array processors, secure microprocessors, application-specific integrated circuits (ASICs), and/or other digital processing devices. Such digital processors may be contained on a single unitary IC die, or distributed across multiple components.

As used herein, the term "network interface" refers to any signal, data, and/or software interface with a component, network, and/or process. By way of non-limiting example, a network interface may include one or more of FireWire (e.g., FW400, FW800, etc.), USB (e.g., USB2), Ethernet (e.g., 10/100, 10/100/1000 (Gigabit Ethernet), 10-Gig-E, etc.), MoCA, Coaxsys (e.g., TVnet™), radio frequency tuner (e.g., in-band or OOB, cable modem, etc.), Wi-Fi (802.11), WiMAX (802.16), PAN (e.g., 802.15), cellular (e.g., 3G, LTE/LTE-A/TD-LTE, GSM, etc.), IrDA families, and/or other network interfaces.

As used herein, the terms "node", "neuron", and "neuronal node" are meant to refer, without limitation, to a network unit (e.g., a spiking neuron and a set of synapses configured to provide input signals to the neuron) having parameters that are subject to adaptation in accordance with a model.

As used herein, the terms "state" and "node state" is meant generally to denote a full (or partial) set of dynamic variables used to describe node state.

As used herein, the term "synaptic channel", "connection", "link", "transmission channel", "delay line", and "communications channel" include a link between any two or more entities (whether physical (wired or wireless), or logical/virtual) which enables information exchange between the entities, and may be characterized by a one or more variables affecting the information exchange.

As used herein, the term "Wi-Fi" includes one or more of IEEE-Std. 802.11, variants of IEEE-Std. 802.11, standards related to IEEE-Std. 802.11 (e.g., 802.11 a/b/g/n/s/v), and/or other wireless standards.

As used herein, the term "wireless" means any wireless signal, data, communication, and/or other wireless interface. By way of non-limiting example, a wireless interface may include one or more of Wi-Fi, Bluetooth, 3G (3GPP/3GPP2), HSDPA/HSUPA, TDMA, CDMA (e.g., IS-95A, WCDMA, etc.), FHSS, DSSS, GSM, PAN/802.15, WiMAX (802.16), 802.20, narrowband/FDMA, OFDM, PCS/DCS, LTE/LTE-A/TD-LTE, analog cellular, CDPD, satellite systems, millimeter wave or microwave systems, acoustic, infrared (i.e., IrDA), and/or other wireless interfaces.

It may be desirable to guide the attention of remote robotic devices within an arbitrarily configured environment, such as, the environment which the robot may not be familiar with (e.g., a search and rescue robot) as opposed to the environment which the robot has a detailed knowledge of, e.g., assembly line robotic manipulator arm. Attracting attention of the robot may be particularly useful without being required to have detailed knowledge of intricacies of the robot internal designs, continuing remote operation of the device, and/or develop specialized software applications for controlling robotic devices.

Irradiation (e.g., illumination) cast upon the world itself may indicate to the robot the area where its attention may be desired. By way of illustration applicable to automated aircraft inspection, an external agent (e.g., a human user, a pre-installed beacon, and/or an intelligent robotic controller) may illuminate (e.g., using a beam of light) a portion of the aircraft undergoing inspection in order to indicate to the inspection robot target areas requiring more detailed (and/or immediate) inspection. The agent may modify the spectral power distribution of a portion of the environment in order to draw attention of the robot. The robot may use these properties to guide its attention.

The robot guidance may be aided by way of an additional signal transmitted by the agent to the robot indicating that the object has been illuminated and attention switch may be required. Upon receiving the additional signal, the robot may initiate a search for the signal reflected by the illuminated area requiring its attention. For example, a beam of light may be used in order to indicate the surface, object, and/or activity that should be attended to and/or acted upon by the robot. The additional signal may be transmitted using a separate button function of the flashlight. The additional signal may indicate to the robot a type of action that may need to be performed once the robot identifies the illuminated area. For example, a single click may indicate a cursory examination and/or taking of a digital picture, while a double click may be indicative of a more thorough inspection, comprising, for example, recording of an ultrasonic and/or high resolution microscopic imagery. Upon detecting the illuminated object and receipt of the context indication (e.g., the additional signal), the robot may develop an association between the two events and the inspection task. The task association data may be stored by the robot for future use in order to be able to initiate the task in the future.

One or more processes and/or architectures for sharing such state information among a plurality of users are disclosed herein. In some implementations, a cloud-based repository 1206 of robotic device "brain images" (e.g., neural network state information) is introduced. Users may access the cloud repository (such as under a subscription, per-access, or other business model) and browse available brain images created by other users. Brain images may also be offered for purchase via the repository in an online "app" store model. Other related content such as user-created training related media (e.g., a video clip of "how I trained my robot" or the like) may be available through the repository and social forums and links.

In some implementations, a cloud-based repository may store pairs of contexts and attended regions. These pairs may comprise signals provided to the robot for its learning in real time, and/or may be applied at other times to other robots. This implementation may allow another (or the same) robot with a different internal state (a different "brain image") to apply the learning without overwriting its previously learned information.

Exemplary implementations are now described in detail. It will be appreciated that while described substantially in the context of autonomous robotic devices, the present disclosure is in no way so limited. Rather, the innovation is contemplated for use with any number of different artificial intelligence, robotic, and/or automated control systems.

Figure 2:
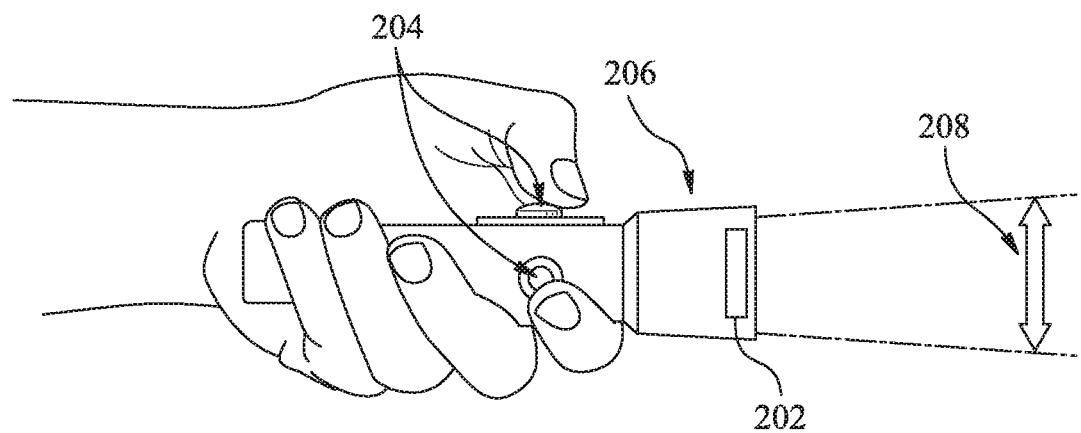
FIG. 2 is an illustration depicting the attention spot light useful with the game of FIG. 1, according to some implementations.
Figure 3:
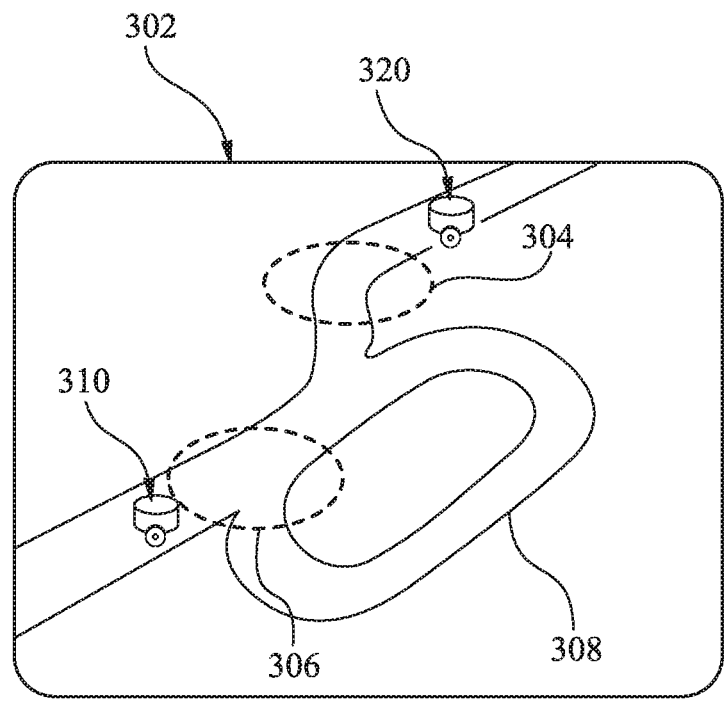
FIG. 3 is an illustration depicting guiding of robotic toys of FIG. 1 using the attention spot light, according to some implementations.

In some implementations, a robot racing game may be developed as entertainment, as illustrated in FIGS. 1-3. Two (or more) players 102, 104 may compete in racing the toy cars 110, 120, using the attention spot light 106_1, 106_2. The attention spot light 106 may comprise a flashlight configured to radiate light beams of light that comprise a different characteristic. In some implementations, the characteristic may comprise wavelength, spectral composition, and/or polarization. In some implementations, the flashlight 106 may employ a filter 202 in order to adjust spectral characteristics (e.g., color) of the beam 204, of the spot-light device 206, as shown in FIG. 2.

The spot light device 206 may be utilized for guiding the moment in time, location, and/or size of region that ought to be attended to by the robot. In some implementations, the spot-light device 206 may comprise a hand-held device configured similar to a laser pointer and/or flashlight. In one or more implementations, the device 206 may comprise additional functionality, such as for example, one or more of (i) a programmatic pairing link with the attention block of the robot (e.g., the robotic car 110 of FIG. 1); (ii) adjustable beam-width in order to control the extent of the attended (target) region; (iii) one or more buttons configured to provide supplementary contextual information to the robot; (iv) a wireless communication block configured to communicate to the robot non-visual information (e.g., button presses); (v) a feedback indicator configured to providing a confirmation that the context was received by the robot; and/or other functionality. In some implementations, the context button 204 may be paired with the beam 208 generation in order to convey to the robot "act now on this" and/or "reinforce this label right here and now" tasks. In some implementations, the feedback indicator may comprise a vibration device, an audible indication, and/or a visual indication (LED a light and/or a mini-display).

Beams of different light may be used, for example, to attract attention (e.g., guide) of a particular robotic cars 110, 120. Individual robots 110, 120 may be characterized by a sensing field of view 112, associated, for example, with the aperture of the robot's sensor. In some implementations, the sensor (not shown) may comprise a digital camera comprising a lens and an imaging array. Examples of an imaging array may include one or more of a charge coupled device (CCD), CMOS device, an active-pixel sensor (APS), and/or other imaging array.

In some implementations, in the game mode the beam characteristics may be intentionally configured to be the same or similar to one another. Such configuration may enable the players to distract opponent's robot when the other player is not actively guiding it. However, when lights of both flashlights are present in the robot's visual field 112, its own players light source may overpower the contribution by the opponent's flashlight.

At individual moments in time, a sensing device of the robot may process the data within the visual field 112. In some implementations, such data may comprise a sequence of digitized image frames. Color processing algorithms implemented by the robots 110, 120 may be configured to identify a region within the frames that may be illuminated by the external attention-trigger apparatus (e.g., the flashlight 106). The detected beam footprint 114 may be subtracted from the frame data so that the color merely allocates the region of interest. At one moment, a player may select a door at the far end of the room, instructing its robot (e.g., the robot 110) to proceed to that location. Accordingly, selecting an object within the environment by placing the flashlight beam onto the object may be referred to as providing structured spatial contextual information to the robot. At a later moment, the player may shine the light on the opponent's robot (e.g., the robot 120). In some implementations, selecting the opponent's robot may act as a command to that robot (e.g., the robot 120) follow the player's own robot (110). In order for the robots 110, 120 to be able to recognize the context (e.g., the appearance of the beam footprint 114 in their view field 112) and to perform appropriate tasks the robots may comprise processing apparatus operating computer executable code (i.e., program) implementing desired functionality. In some implementations, the processing apparatus may comprise neuromorphic computerized apparatus configured to operate spiking neuron network, as described in detail with respect to FIGS. 11A-11C, below. The program may use the union of the command ("light on robot") and the detection of a visual feature in the attended region (e.g., "detect robot"), to initiate the following behavior. Shining a light on another object (e.g., the door) may not cause the robot to follow the door, because there is no robot detected in the selected region.

FIG. 3 illustrates one example of a track for use with the attention spot light and the car race game. In the absence of a controller, the robots 310, 320 may follow the track 302 in front of them. Autonomous toy robots make random choices when the track forks 304, 306. When a player guides the robot's attention towards (i) an upcoming section of the fork (e.g., the fork 304) using the attention spot light described above, the player may bias the robot's choice to favor the guided route. In this manner a player may prevent a robot from getting stuck in a side loop 308, or may lure an opponent's robot into such a loop.

Figure 4:
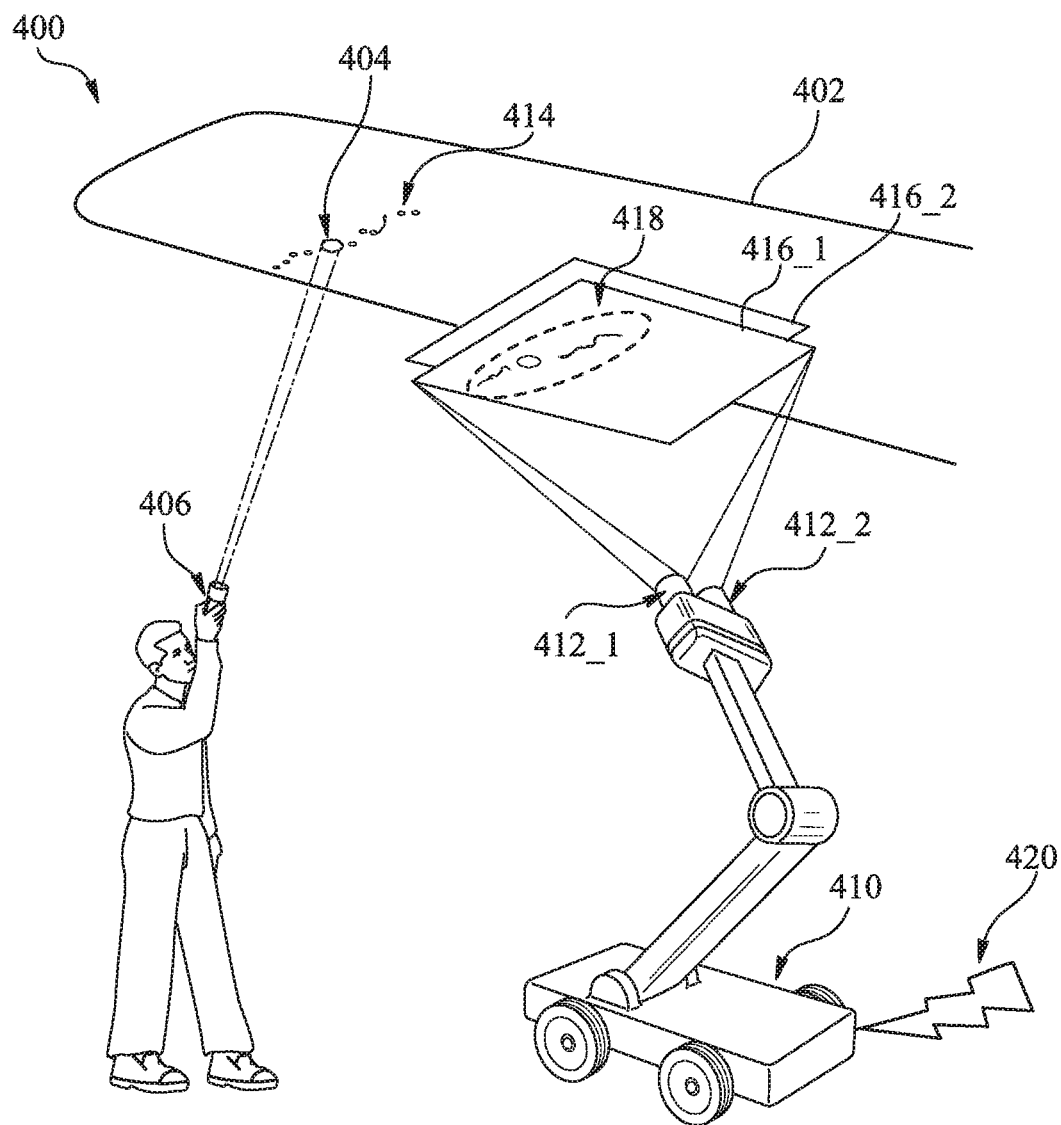
FIG. 4 is an illustration depicting a robotic aircraft inspection apparatus comprising attention spot light, according to some implementations.

In accordance with some implementations, a robotic system 400 may comprise a robotic apparatus 410 configured to inspect an aircraft airframe 402 and/or power plant (not shown) for cracks, as illustrated and described in detail with respect to FIG. 4. In some implementations, the robot 410 may be assigned a task of locating candidate regions 414 that may require repair and/or further inspection as a part of regular aircraft maintenance over time. During initial deployment, an operator may guide the robot 410 (e.g., position aperture 416 of the robot sensor 412) to a location 414 of known or suspected damage. In one or more implementations, the guidance may be effectuated by using a spot-light device 406 (e.g., the device 206 of FIG. 2). The spot-light 406 may illuminate a portion 404 of the area 414 that may require inspection. The operator may be conveying to the robot the message "this kind of region is worth inspecting." Similarly as in the racing game implementations described with respect to FIGS. 1-3 supra, the spot-light 406 may comprise one or more buttons (e.g., the buttons 204 in FIG. 2), and a wireless communications block configured to communicate a context indicator to the inspection robot 410. The spot-light 406 may comprise a feedback display configured to provide a confirmation to the operator that the inspection robot 410 has received task instructions and/or commenced task execution.

Responsive to the footprint 404 being within the robot sensor aperture 416, the robot 410 may assess the region in the vicinity of the beam footprint and/or provide a report to the operator. In one or more implementations, the report may indicate the outcome of the inspection, an intensity score, a pass or fail, a confidence score, a summary of key properties measured, or why the inspection was not performed, if it was not, and/or additional information. In some implementations, based on the preferences of the user and/or the preferences of a subscribed cognitive channel, the robot 410 may collect additional sensory information about the surrounding of the footprint.

A robot may have one or more cognitive channels associated with the same or different tasks (and/or sub-tasks). A given cognitive channel may comprise mapping of a sensor state onto an action. In some implementations, the mapping may be based on: 1) selecting sensor states that are more important 626, 646, 666, 686; and/or 2) determining how to act on the contents of the selected sensor state 628, 668.

In some implementations, an action may comprise an internal command (e.g., "keep searching"). In some implementations, the internal command comprises low dimensional signals (even discrete commands).

Based on additional sensory data, the robot 410 may generate a context associated with the region. The context may comprise information in its primary sensory domain ("ultrasound context"), other sensory domains ("camera context"), and/or other kinds of data. Examples of other kinds of data may include one or more of "recent actions initiated", "recent commands received", "my relative location with respect to this plane", and/or other kinds of data. In one or more implementations, the context may comprise raw and/or processed (e.g., using contrast enhancement and/or edge tracing to detect cracks) portion of the frame 418 comprising the area of potential damage. In one or more implementations, the processed sensory data may be stored as the activity of spiking sensory neurons represented as a vector of activity across regions and features by means of the aggregate impulse activity or a code based on relative timing of impulses.

In one or more implementations, the spot-light 406 and the inspection 412 may employ different technologies. Examples of such different technologies may include one or more of visible light, ultrasonic, infrared, ultraviolet, x-ray, and/or other technologies. In some implementations, the spotlight may utilize visible light, while inspection sensor 412 may perform x-ray-based non-destructive test (NDT).

In some implementations, the data (e.g., the digitized frame 416) obtained responsive to the spot-light operation, may be offloaded via a communications link to a remote processing resource (e.g., a remote server).

The stored context may be subsequently used to train the other inspection systems and/or other robots 410. With sufficient training, the robot 410 may be able to locate other potential areas of damage without relying on the human controller. Sufficient training may include inspecting a number of features 414 for signature of damage and/or collecting contexts associated therewith. In some implementations, the robotic inspector 410 may generalize and apply the knowledge gained upon inspecting one type of airplanes, to other same airplane types previously not serviced by the robot. By way of illustration, the robot may determine, based on the history record of inspected areas, that areas where wings couple to the fuselage, and/or areas surrounding windows and cockpit may require frequent inspection, that when it has found a problem at a particular window it should also check other windows that share common causes of wear, that when it is particularly cold, it should also check additional regions.

Figure 4A:
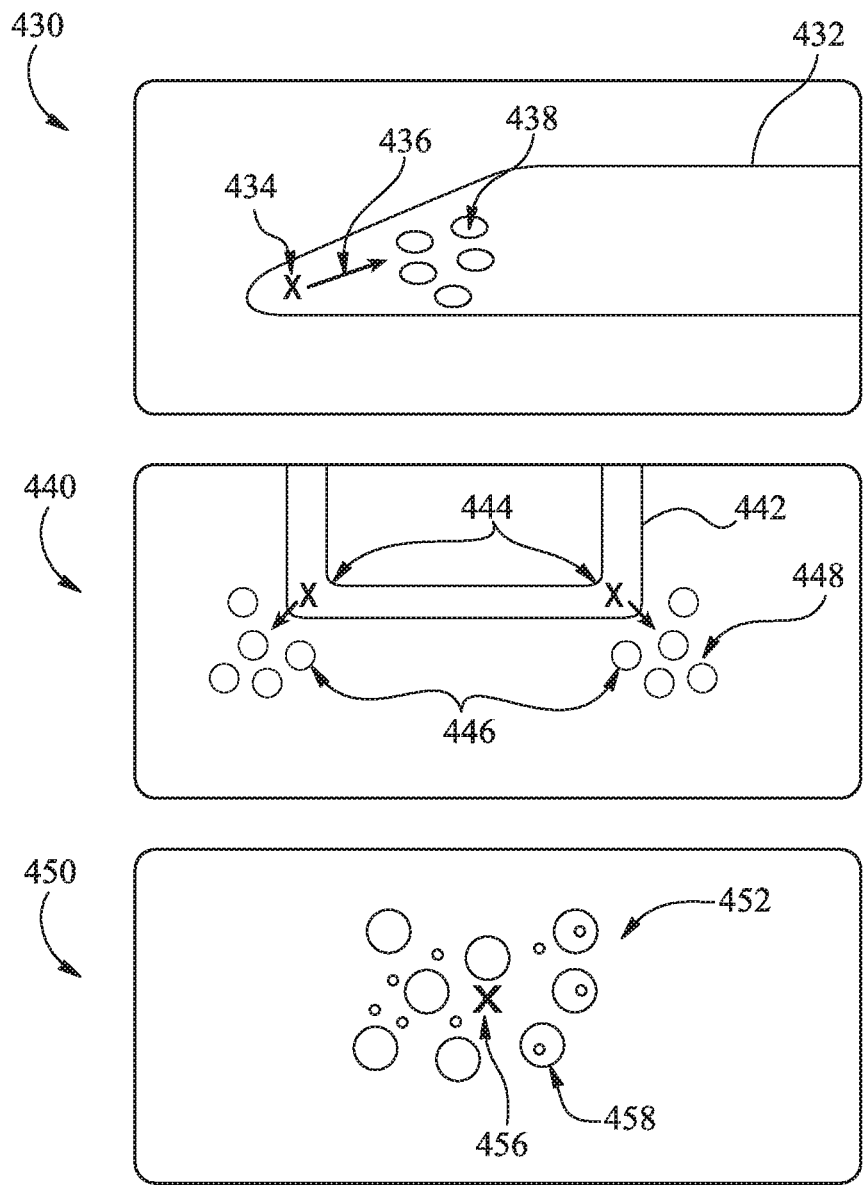
FIG. 4A is an illustration depicting impact of a feature on attention of a robotic device, according to some implementations.

FIG. 4A illustrates an impact of a feature on attention of a robotic device. The panel 430 depicts a view (from the robot's perspective) comprising the wing of an airplane 432. The view comprises a learned feature 434, which may have a strong response proximate the tip of the airplane wing and which may have been previously learned by the robot. The arrow 436 indicates that the attention of the robot is directed to regions containing the circles, denoted 438 in FIG. 4A. The presence of strong activity at location 434 in the learned feature layer may increase the attention at location 438, ultimately emphasizing the features of the image context that are located at 438. The relative mapping from the feature 434 to the attended region 438 may be learned by the robot from the previous robotic contexts.

The panel 440 illustrates a view from the robot's perspective comprising the bottom half 442 of a window. Features 444 disposed proximate the corners of the windows may have been learned by the robot. The arrows 446 indicate that the attention of the robot is directed to regions containing the circles 448. The relative mapping from learned feature to the attended region may have been learned from previous robotic contexts.

The panel 450 illustrates a view from the robot's perspective comprising texture pattern 452. An arbitrary characteristic (feature) of the texture pattern 452 that has been learned by the robot, and its centroid, may be specified by the arrow 456. There is no arrow because the attended region overlaps with the learned feature, within the region of the bumps. The circles 458 denote the locations of increased attention due to the presence of the feature 456. The relative mapping from learned feature to the attended region may be learned from previous robotic contexts.

Figure 5:
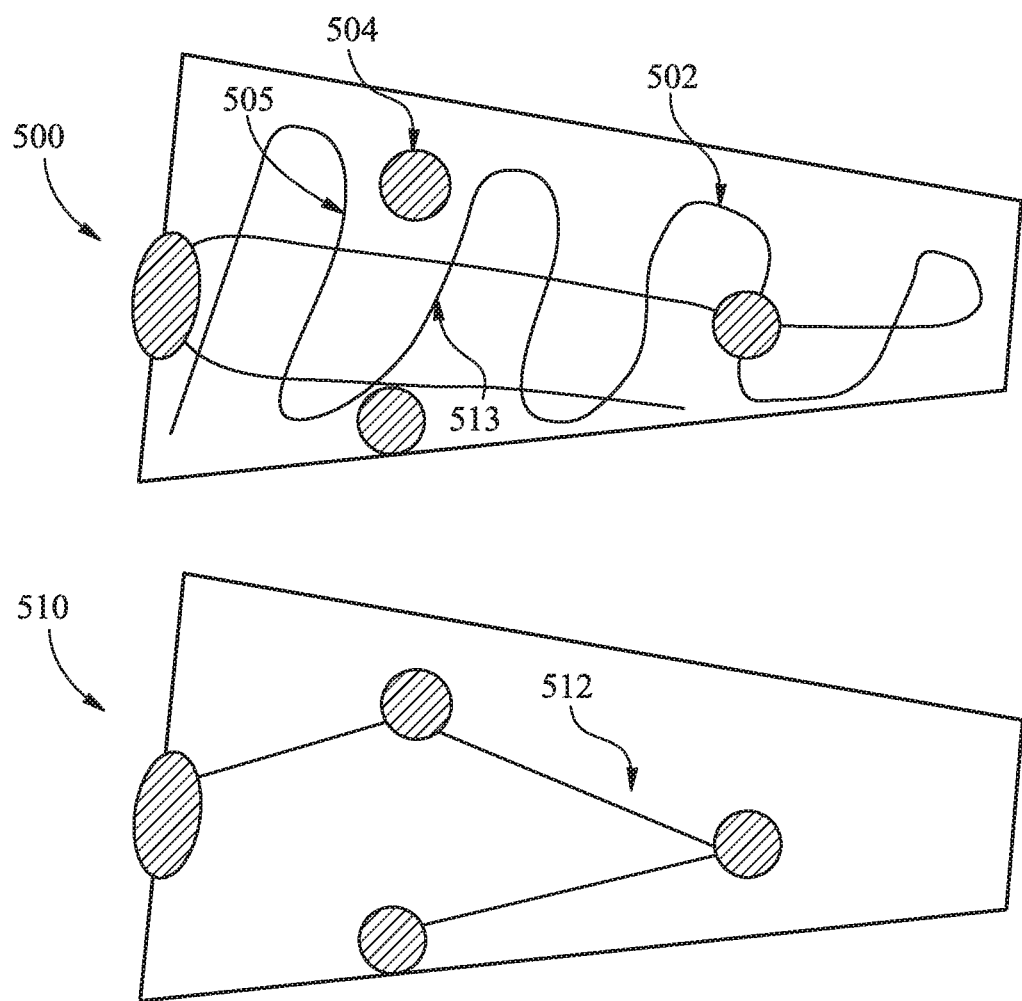
FIG. 5 is an illustration depicting exemplary trajectories of the robotic aircraft inspection apparatus of FIG. 4, according to some implementations.

In some implementations, attention spot-light methodology may reduce inspection duration as illustrated in FIG. 5. The panel 500 in FIG. 5 represents a conventional grid-like search pattern that may be used by a pre-programmed inspection robot (e.g., the robot 510 of FIG. 4) configured to inspect an airplane wing. While the inspection may require evaluation of a few potential problem areas 504, denoted by dark shapes, the route 502 of the robot camera may extensively cover other areas that may not require detailed inspection at this time. When the search grid is too coarse (e.g., space between adjacent survey path is wider than size of the defective area illustrated by the path 503, 505 in FIG. 5), one or more areas of potential damage may be missed, as shown by the area 504 in the panel 500. If a grid search is exhaustive, the duration of a complete search may render it infeasible to perform frequently and/or to identify new problems in a timely manner.

The panel 510 in FIG. 5 represents a spot-light-aided search pattern 512 obtained by the robot with the aid of the attention spot-light 406 of FIG. 4. The context-aided inspection route 512 may be shorter than the pre-programmed route 502 leading to a shorter inspection time and/or reduced inspection cost. The use of context aided route may help ensure that all of the potential areas of damage are covered by the inspection route 512.

The robots may learn to adjust their attention based on the mapping between the learned feature and a particular task at hand. Attention may serve one of more of the following purposes: (i) to determine which features to select in order to determine the next task, (ii) to determine which features to select in order to optimally complete the current task, and/or other purposes. In one or more implementations, attention may be described as the impact of learned features X, upon other robotic features F given a particular task state T. Learning may determine the function which generates a vector of scalars A, that adjusts the gain of every feature in F, typically, though not necessarily, based on its spatial position in the map.

$$A = f(X, T) \quad \text{(Eqn. 1)}$$

$$F = A*F \quad \text{(Eqn. 2)}$$

When a robot performs two tasks, then (2+1) mappings may be learned. These mappings may include the mapping of attention during search which determines where the robot should look next, the mapping of attention when performing an x-ray which optimized the robots accurate assessment, and/or other mappings. Attention may be deployed by the robot when determining which task to perform next. In this example, it may be the choice of weather to keep searching or to image at the current location. A successful learning algorithm may use the context to select the region of the image to attend to that a human expert would have indicated, had they been there to guide the robot at each task.

Figure 6A:
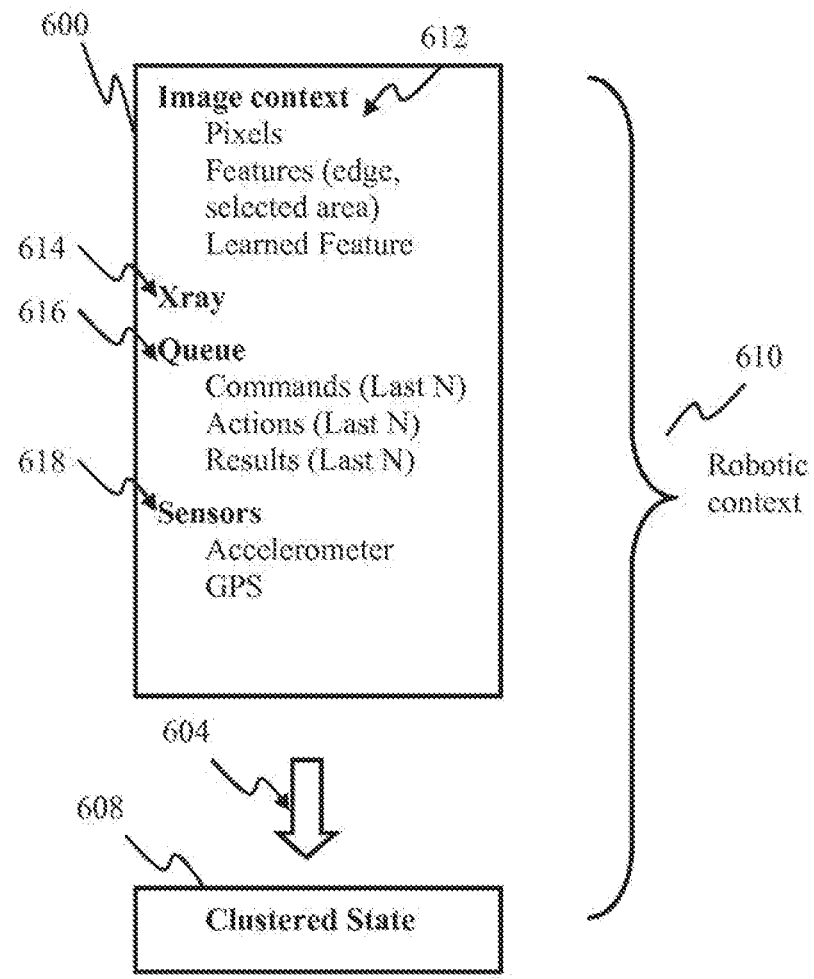
FIG. 6A is a block diagram illustrating robotic context of the disclosure, according to some implementations.
Figure 6B:
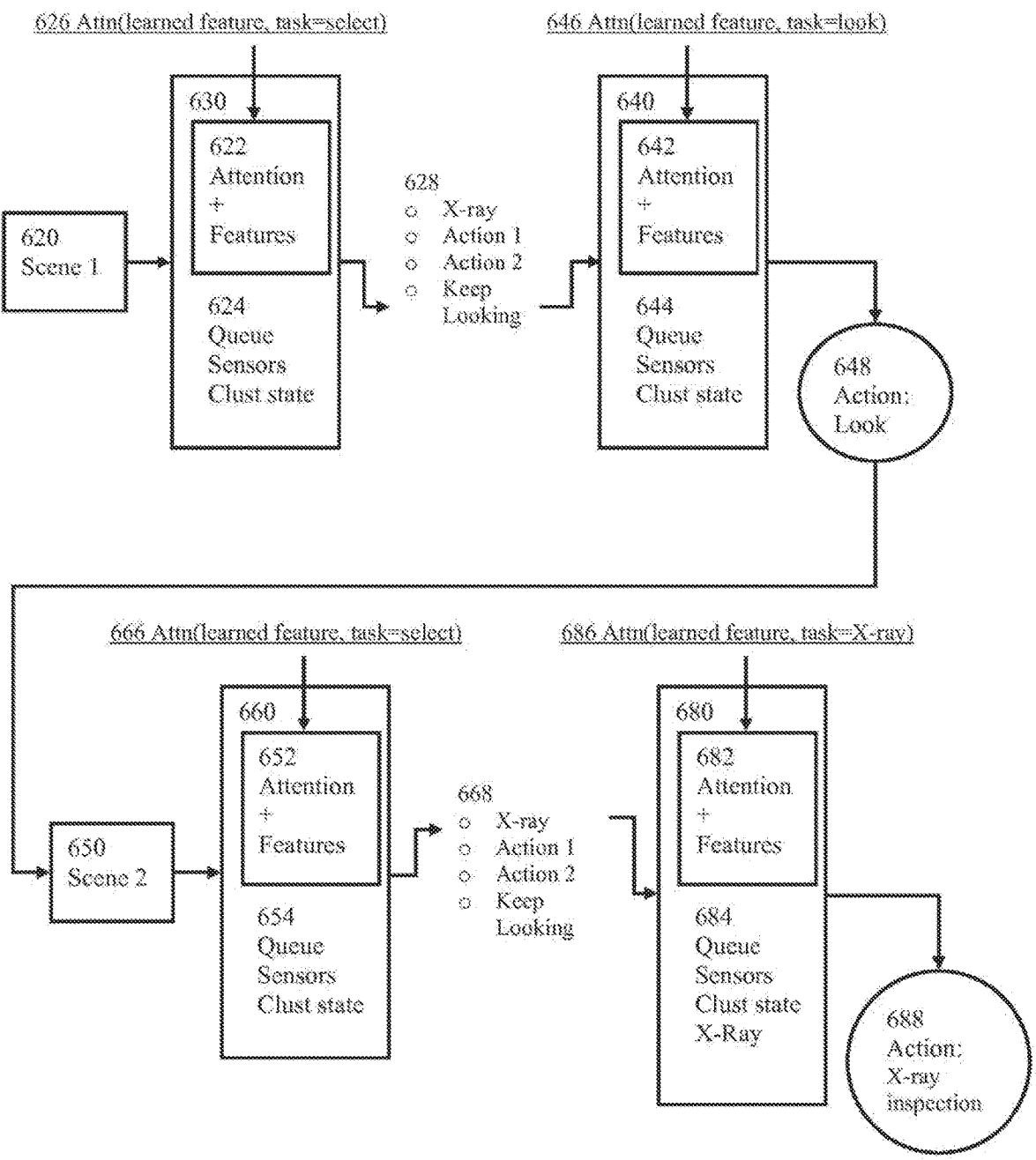
FIG. 6B is a graphical illustration depicting robotic context generation, according to some implementations.

FIG. 6B illustrates robotic attention guided by the robotic context on a trained robot, in accordance with one or more implementations. The flow of behavior of a robot may include selecting a task to keep looking 628, choosing to look at a particular region 646, selecting to perform a task of doing an x-ray inspection 668, choosing to perform the x-ray inspection a particular way 656, and/or other operations. An attention signal may be provided to the robot. In some implementations, the attention signal may be effectuated using the spot-light 206, 406 described above with respect to FIGS. 2 and 4. In some implementations, such as depicted in FIG. 6B, the attention 626, 646, 666, 686 may be determined by the robot based on its context 630, 640, 660, 680 before attention. The attention determination may be based on, for example, the learned feature and task indication. In one implementation, a task may be to select in the attention signal 626 of FIG. B.

A scene 620 may be provided to the robot. The scene 620 may be related to the robot's environment and/or an object to be inspected. The robot context 630 at this stage may include additional components 624. In some implementations, additional components 624 may include one or more of sensor data, command queue, clustered state of the robotic context, and/or other components. In one or more implementations, the clustered state of the context 624, 644, 654, 684 may comprise a single state variable derived from all other aspects of the robotic context. In some implementations, the clustered state may be a low-dimensional representation of the robotic context, as computed by an unsupervised learning algorithm. The robot may utilize scene data to derive one or more features (e.g., the feature 418 of FIG. 4) using various processing methodologies. The attention indication 626, 646, 666, 686 may be combined with the features to form an updated representation of the features 622, 642, 652, 682 reflecting the impact of the attention. The robotic context 630, 640, 660, 680 after the impact of attention may be used to select the next action 628, 668 and/or to provide the best sensory data to guide the performance of a particular action 646, 656. A different cognitive channel may be subscribed to for individual tasks, such as in a case where additional sensory channels are included. The different cognitive channel may include 684, which may comprise X-ray features within the robotic context 680.

In some implementations, learning by a robot may be aided by an error signal. The error signal may convey a difference in the robots internal attention algorithm, the region selected by the user, and/or other information. The error signal may enable the robot to incrementally improve an estimation of the "correct" region to attend to in an online manner. Off-line learning may be used to minimize attentional error across a database of actions and/or contexts associated with individual actions.

In some implementations, a classification of the task to perform when selecting an action may be based on the current context. The task may comprise an N-way classification given labeled data. In some implementations, labels may be generated as follows:
1) Robot is instructed by expert to do X. X and context are bound as a positive example.
2) Robot attempts to do X, and expert changes robots behavior. X and context are bound as negative example.
3) Robot attempts to do X, and expert does nothing, Expert is confirmed to be present and engaged. X and context are bound as a positive example with the passive flag.
4) Robot does not perform action, and random background sampling occurs during exploration. If expert is present and does nothing, then context is bound as a negative example to all task X, Y, Z with the passive flag. This is also referred to as the noise distribution for action detection.

Some algorithms may group training samples into one of two groups: positive and negative examples. Some algorithms may treat passive and actively bound samples differently, for example, by ignoring passive training samples or weighting them differently. In task selection, both forms of learning may occur. That is, learning of which features to attend to in order to perform the task, as well as the mapping of the attended features to the selected task may occur, in some implementations.

The learning store may provide a format converter between robotic contexts of the same channel that differ by resolution of learned features and image features. In some implementations, the converter may use interpolation, up-sampling and/or down-sampling, super resolution, density estimation techniques, and/or other operations to approximate the experience that another robot would have had, had it been in the same context of the robot that actually recorded the context action sample. In some implementations, interpolation may be performed between different kinds of sensors and image features.

Some implementations relate to a method that enables users of robotic devices to have the ability to share content related to the training of such robotic devices. In various implementations, a user may extract the state of a neural network and/or other useful training-related information directly from the device. An artificial mind and its traits may be copied, stored, and later retrieved, as described in detail with respect to FIG. 12 below. This state information may be shared with other users. A user may download such stored state information (whether from networked or cloud storage, or in a peer-to-peer (P2P) fashion) and apply it to a second neural network, effectively duplicating the first neural network. The user may apply the experience of learning by one robot to operation of another robot by transferring training examples in the form of pairs of context 600 and valid command 702, where one particularly important command is paired with attentional allocation 734. The robot may update its internal function based on the concatenation of its previous training examples, and those obtained from the cloud, or it may be scheduled to stochastically update from its training samples in an online fashion, so that each exposure of a training example results in a small change in the robot's total learned state.

Figure 12:
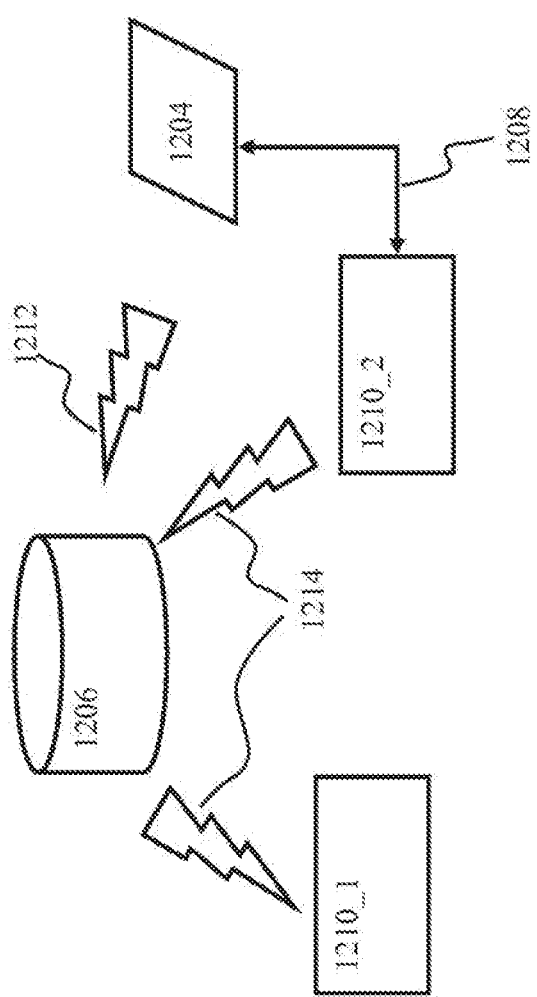
FIG. 12 is a functional block diagram illustrating a cloud server repository, according to some implementations.

State information may be shared among a plurality of users. In some implementations, such as illustrated in FIG. 12, a cloud-based repository 1200 of robotic device "brain images" (e.g., neural network state information) may be introduced. The repository may comprise cloud server depository 1206. In FIG. 12, one or more remote user devices 1210 may connect via a remote link 1214 to the depository 1206 in order to save, load, update, and/or perform other operation on a network configuration. The one or more remote user devices 1210 may further interface with a local user computerized device 1204 via a local link 1208 in order to facilitate learning configuration and software maintenance of the user device 1210. In one or more implementations, the local link 1208 may comprise a network (e.g., Ethernet), wireless (e.g., Wi-Fi, Bluetooth, infrared, radio, and/or other wireless), serial link (e.g., USB, Firewire, and/or other serial links), and/or other links. The local computerized device 1204 may communicate with the cloud server depository 1206 via link 1212. In one or more implementations, the local computerized device 1204 may comprise a tablet and/or a smartphone device. In some implementations, the local computerized device 1204 may comprise the indication providing device (e.g., the attention spot light 106, 206, described above with respect to FIGS. 1-2).

In one or more implementations, links 1212 and/or 1214 may comprise an internet connection effectuated via any of the applicable wired and/or wireless technologies. Examples of wired and/or wireless technologies may include one or more of Ethernet, WiFi, LTE, CDMA, GSM, and/or other technologies.

The connectivity structure of the exemplary computerized apparatus 1150, the user interface device 1202, and/or the cloud server 1206, described with respect to FIGS. 11C and 12, respectively, below, may be designed to aid in fostering a social environment in which the computerized neuromorphic apparatus 1150 are trained. Through options in the training application, users may access content shared by other users. This content may include media related to the training of the computerized neuromorphic apparatus 1150 (e.g. videos, pictures, collected sensor data, wiki entries on training techniques/experiences, forum posts, and/or other media), brain images, third-party/homebrew modifications, and/or other information. Users may form user groups to collaborate on projects and/or focus on specific topics. Users may form user groups to focus on collective formation of a brain image (somewhat akin to extant distributed gaming interaction). In some implementations, a user may cross-link to groups and content on third-party social media websites. Third-party social media websites may include one or more of Facebook®, Twitter®, and/or other third-party social media websites.

Users may subscribe to groups with notifications of new training examples for a particular cognitive standard that is compatible with their robot, or reports that validate that recently available training sample improve performance on a particular robotic task. In some implementations, notifications may be sent directly to the robot via a machine-readable format or RSS feed, with automatic updating according to the robotic owner's preferences.

FIG. 6A illustrates some implementations of robotic context comprising clustered state. The panel 600 may comprise one or more information categories accessible to a robot (e.g., the inspection robot 410 of FIG. 4). The information 600 may comprise context related to the imager 412_1, comprising, for example, raw pixel data, features detected within the image (e.g., the feature 418, edges, etc.). The information 600 may comprise context related to another imager (e.g., the X-ray imager 412_2), sensor data, and/or one or more queues configured to store last several commands received, actions performed, and/or results stored by the robot. One realization of the command/action/result data portion is presented in Table 1, where commands/actions/results are denoted using respective identifier numbers.

In one or more implementations, the information 600 may be processed using, for example, a clustering technique 604. The output of the clustering technique may comprise a clustered state data 608, comprising either a single ID and a confidence of belonging to that state, or a low dimensional vector of values that are a more interpretable summary of the high dimensional robotic context.

TABLE 1

|  | n-4 | n-3 | n-2 | n-1 | N |
|---|---|---|---|---|---|
| Command | 162 | 240 | 162 | 162 | 162 |
| Action | 762 | 1041 | 767 | 762 | −1 |
| Result | 314 | 315 | 314 | 315 | −1 |

FIGS. 7A-9D describe exemplary methods that illustrate various implementations of guiding attention of the disclosure.

Figure 7A:
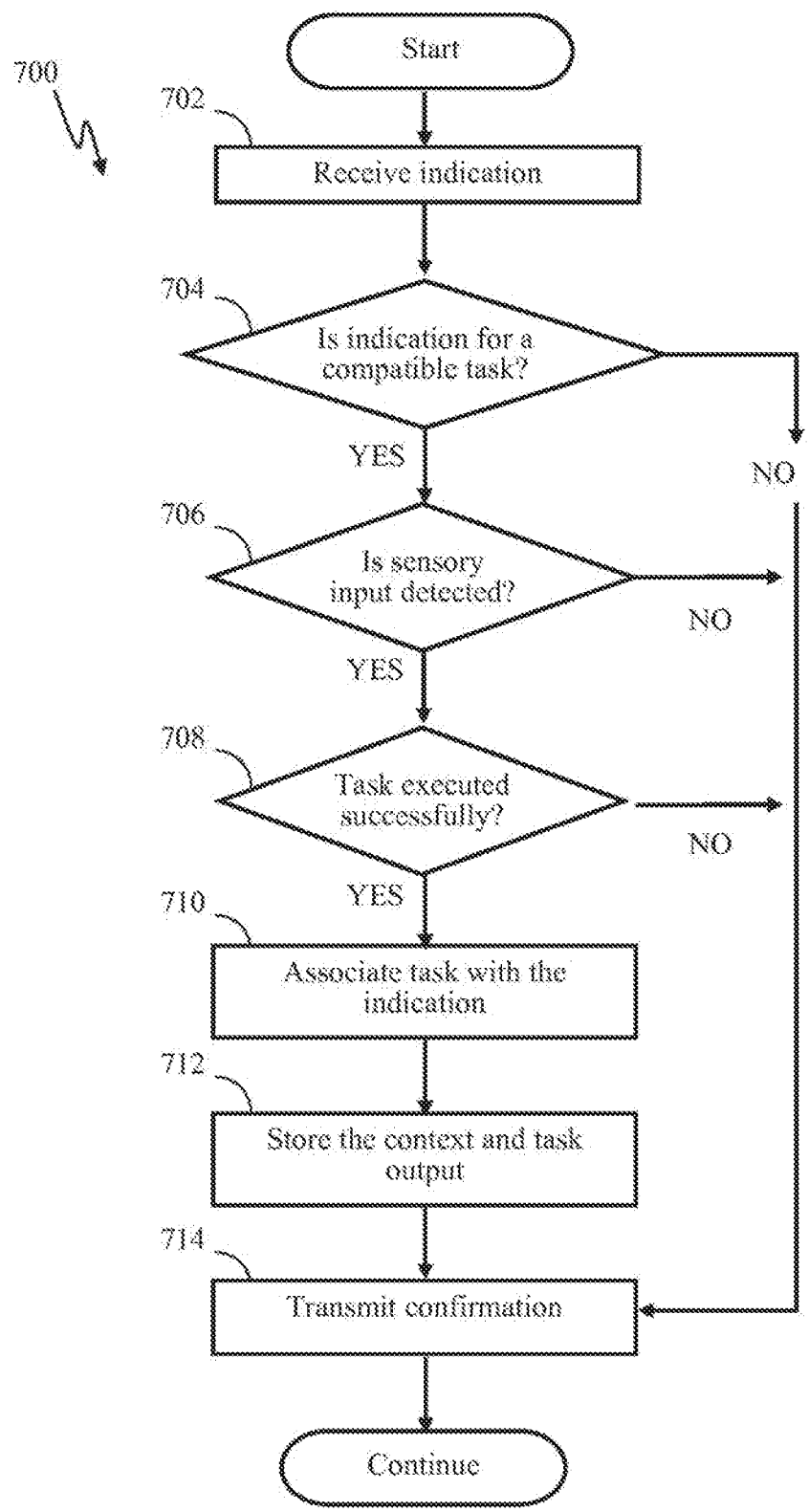
FIG. 7A is a logical flow diagram illustrating operation of the robotic apparatus of FIG. 4, in accordance with some implementations.

FIG. 7A illustrates a method of operating a robotic apparatus (e.g., the apparatus 110 of FIG. 1 and/or inspection robot 410 of FIG. 4), in accordance with some implementations.

At step 702, a task indication and/or a command may be received. In some implementations, a task indication may include one that is similar to or the same as that described below with respect to step 734 of FIG. 7C.

At step 704, the robot may verify that the indication comprises a known and/or a compatible task. Responsive to a compatible task indication being received, an acknowledgment feedback may be transmitted to the agent. If the task is deemed incompatible by the robot, the method may proceed to step 714 where a feedback indicative of the incompatible task may be communicate back to the agent. Responsive to receipt of a task notification, prior to performing the task, the robot may save the state of its recent context, which is passing through a circular memory buffer. This may be referred to as the "robotic context".

The nature of the robotic context may depend on the cognitive platform of the robot. A robotic context may include one or more of the state of the robot sensors, other internal states of the robot, a recent history of commands given to the robot, actions taken by the robot, the result of those actions, and/or other robotic contexts. An exemplary robotic context 610 is illustrated in FIG. 6A. Responsive to a user issuing a command (e.g., to pick up a particular object), a snapshot of the robotic cognitive state 600 may be saved. The cognitive state may be paired with the command thereby generating the context. The cognitive snapshot 600 may comprise image context (e.g., pixels, features, and/or learned features), as illustrated in FIG. 6A. The image context may be mapped into a spatial image domain. Pixel context may comprise the RGB values of the last acquired digital image, prior to the command. The image may be shifted by a constant offset in time, according to the channel. In some implementations, two or more images may be acquired to suit the needs of sampling the context at the moment that the user issues the command, and the moment that the secondary imaging device (e.g., x-ray and/or device 412_2 in FIG. 4) is activated. The image context 612 may comprise features associated with the current state of the robots low-level image processing. These features may comprise, for example, the results of operating algorithms for edge finding and/or location extraction of the attention spotlight signaled by the user.

The image context 612 component may comprise a spatial map that results from one of the learned features that are being dynamically updated by the robots. In some implementations, the map may be implemented via a template applied to the image features. In some implementations, the learned feature map may comprise a hierarchy of computed image features. An airplane-inspecting robot may maintain a learned map for windows, wing edges, latches, and cracks. Robotic context may comprise the current state of activation for learned internal states that are not in the image domain, such as from an artificial cerebellum or an artificial hippocampus.

The robotic context 610 may comprise the spatial map of a secondary image domain (e.g., X-ray 614 in FIG. 6A), which, in this example, may be an x-ray image. In a given context, the x-ray image may be in register with image context 612 pixels.

The robotic context 610 may comprise a queue of most recent commands, actions, results 616, and/or other contextual information. Table 1 illustrates one example of such queue, which may comprise a current command, current action, current result, last command, last action, last result, and/or other information. A different instantiation may use a queue of length 1, 2, 10, 100 or 1000.

A command may include a particular discrete category of command issued by the user to the robot, and/or any associated metadata. Such metadata may include a command x-ray a certain location. An action may be the response of the robot. Examples of an action may include one or more of moving to a new location, taking the x-ray, and/or other actions. A result may be the outcome of an x-ray analysis. Examples of an outcome may include one or more of whether or not a crack was found, and/or other outcomes. A robotic context may include the state of the relevant sensors 618 that are not in the image domain. Examples of relevant sensors 618 may include one or more of a GPS, an accelerometer, a thermometer, and/or other sensors. The sensors may have a historical queue, sampled along with the queue of commands, actions and results. The robotic context may comprise a summary of the entire contextual state which is a low dimensional description of the state 608 resulting from a pre-specified clustering or compression algorithm 604. The algorithm 604 may be shared across several robots in the same cognitive channel. Such a clustered state may improve an ability of learning algorithms to make use of common shared states, and/or may facilitate online human monitoring of all the robots belonging to a single cognitive channel.

Responsive to the receipt of compatible task indication, at step 706 the robotic apparatus may begin detection of the sensory input that was indicated by the attention signal. In some implementations, the attention signal may comprise the object irradiation signal, such as the footprint 404 of FIG. 4 and/or the transmission of step 732 of FIG. 7A.

If sensory input associated with the task indication is detected, the method may proceed to executing the task at step 708 of the method 700. If no sensory input is detected due to, for example, the object being out of range of the robot sensor (e.g., the sensor 412 of FIG. 4) the task may be deemed incompatible by the robot, the method may proceed to step 714 where a feedback indicative of the undetectable sensor data may be communicate back to the agent.

Responsive to successful completion of the task, at step 710 the robot may perform an association between the task indication (e.g., the indication received at step 702) and a portion of the data obtained during task execution, thereby augmenting the context action pair as containing a particular label pertaining to the outcome of the action. For example, if an inspection was performed, the outcome of the inspection may be included for subsequent learning algorithms that can make use of it, enabling the system to outperform human attention guidance in the future. In some implementations, a portion of the data obtained during task execution may comprise a processed image taken in the vicinity of the area of attention (e.g., an edge-trace of area 418 of FIG. 4 comprising signature of defects). This post-action context feature may have the capacity to be derived from a different sensor, which may be only conditionally deployed due to its cost in power, time, and/or other constraint. The robot may subscribe to two or more cognitive channels. A first cognitive channel may pertain to exploration, and may contain attention guided to a feature space of a low cost camera. A second cognitive channel may pertain to the use of a costly or time consuming ultrasound imaging system, implementing the same system of context storing, data sharing, and learning. The first context may select between sensory regions to coordinate a search process based on standard image data. The second context may coordinate how long to keep performing a detailed ultrasound imaging process, or what to do if the results of the initial analysis are inconclusive.

At step 712, the context and (a sub-set) of the task output data may be stored by the robot internally. In some implementations, the task data may be off-loaded for storage at an external depository. At various random times, a context may be stored without the user triggering an action. A label may be automatically associated with it, indicating no action was taken. These random samples may be modified or pruned if a user performs an action with a short temporal window. The sample may no longer indicate that no action should be performed, because the latency of sample to the action generation may be the cause of the human operator's latency in processing the world and calculating that the robot should act. The frequency of sampling the context of inaction may be determined by the robots settings, which may be configured by a particular cognitive channel that the robot may subscribe to.

At step 714, a confirmation of successful task execution may be transmitted to the agent.

Figure 7B:
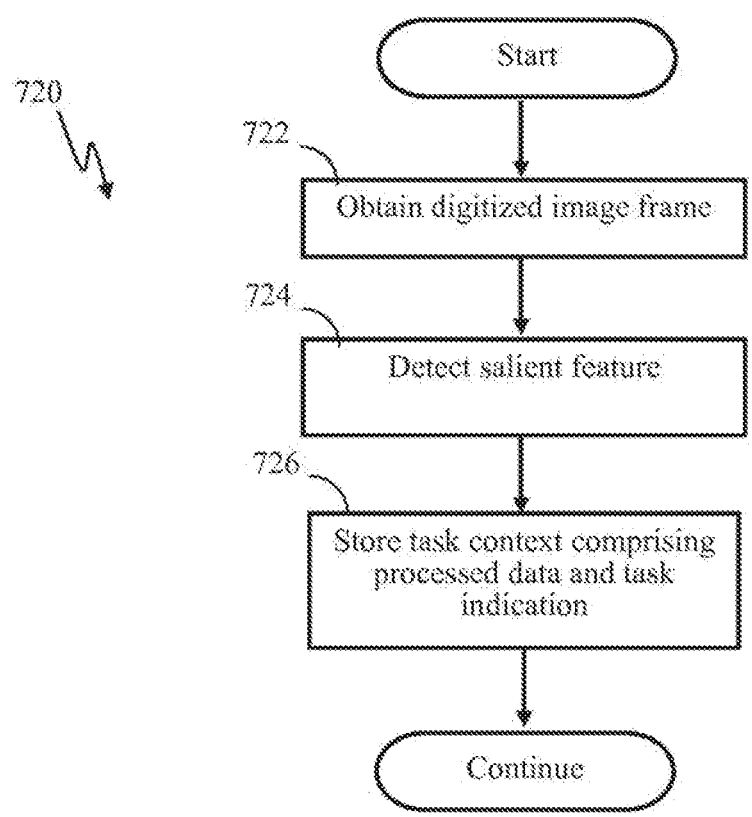
FIG. 7B is a logical flow diagram illustrating storing of task context by the robotic apparatus of FIG. 4, in accordance with some implementations.

FIG. 7B illustrates one implementation of determining of the task context (e.g., the context described with respect to step 712 of method 700).

At step 722, a digitized image of the area (e.g., the area 414 surrounding the object of interest (e.g., the object 404) may be obtained.

At step 724 a salient feature (e.g., the feature 418) within the image (e.g., the image 416) may be detected using a variety of processing techniques. Examples of processing techniques may include one or more of contrast enhancement, edge tracing, spectral and/or spatial transforms, and/or other processing techniques. In some implementations, the salient feature may be detecting using spatio-temporal winner takes all (WTA) methodology described in detail in U.S. patent application Ser. No. 13/548,071, filed Jul. 12, 2012, entitled "SPIKING NEURON NETWORK SENSORY PROCESSING APPARATUS AND METHODS," now U.S. Pat. No. 8,977,582, incorporated supra. In this implementation, the image spectral density parameters (e.g., brightness and/or contrast) may be encoded into pulse latency using spiking neuron network. The encoded spike pattern may be processed using the WTA approach, where the salient features (e.g., the brightest group of pixels) may correspond to pulses with shortest latencies.

At step 726, the task context, comprising for example the task ID of step 702 of FIG. 7 and data pertaining to the salient feature, e.g., the size and/or the location of the feature 414 in FIG. 4.

The context data (e.g., the context stored at step 726 of FIG. 7B) may be subsequently used by the robotic device to perform the task associated with the context. In some implementations, the task execution aided by the stored context may be effectuated in absence of object irradiation by the agent. In one exemplary operational sequence, a new robot may be deployed with no personalized training data. Initial state of the robot network (robotic brain) may be determined by an offline learning algorithm that was informed by one or more previously stored samples of contexts and/or actions performed by other robots. The offline learning algorithm may include machine learning methods for supervised learning like regression, naïve Bayes, random forests, boosting, support vector machines, genetic algorithms, classical artificial neural networks, spiking neural networks, and/or other statistical estimation techniques. When the robot is set to explore or scan the environment, its image sensors may pick up new data that emphasizes components learned from this data. For example, the camera may happen to pass over a joint between the wing and body of the plane, which includes high frequency visual information indicative of a crack. An operator may not be required to indicate to the robot that this region deserves a detailed ultrasound image. Rather, the context may be activated by the sensory data itself, the attention system selects the region worth attending to (the region with the candidate crack), and this may enable the higher-level feature detectors to respond in isolation of background noise. The current context, which may extend to facts beyond the image domain, may be included in determining the next action. An exemplary next action may include taking an ultrasound image or keep scanning elsewhere with a normal camera. Upon having determined that the candidate crack is scored as having a posterior probability of being a crack that is greater than a predetermined and then value-adjusted threshold, the robot would begin the ultrasound. The context may be invoked at two separate points in the robots control process: i) what region in the current context is worth attending to, and ii) if attending to a region that contains a known object type, what action to perform, in accordance with some implementations. Based on the results of the scan, the robot may update its internal state using an online learning algorithm, and/or may send the context action pair back to the cloud storage.

Tasks execution and/or association steps, such as described with respect to steps 724-726 of FIG. 7B, may be performed by a spiking neuron learning network. Such networks may be characterized by an array of synaptic weights and/or neuron state data, as described in detail in U.S. patent application Ser. No. 13/830,398, filed Mar. 14, 2013, entitled "NEURAL NETWORK LEARNING AND COLLABORATION APPARATUS AND METHODS," now U.S. Pat. No. 9,208,432, incorporated supra.

The present disclosure contemplates ability of robotic devices to transfer and/or exchange the stored learned context(s) with other robotic devices in order to facilitate task execution. In some implementations, the transfer may be accomplished by upload/download of SNN image(s) comprising learned context. By way of illustration, an inspection robotic apparatus I may be operated in Seattle to inspect wings of the Boeing 737 aircraft, where it is trained to pay special attention to selected areas A-D. Another inspection robotic apparatus II may be operated in Portland to inspect wings of a different the Boeing 737 aircraft, where it is trained to pay special attention to selected areas E-F. Subsequently, the SNN images of the two robots I, II may be merged to generate a composite network that may be capable of performing inspection of the areas A-F.

Figure 7C:
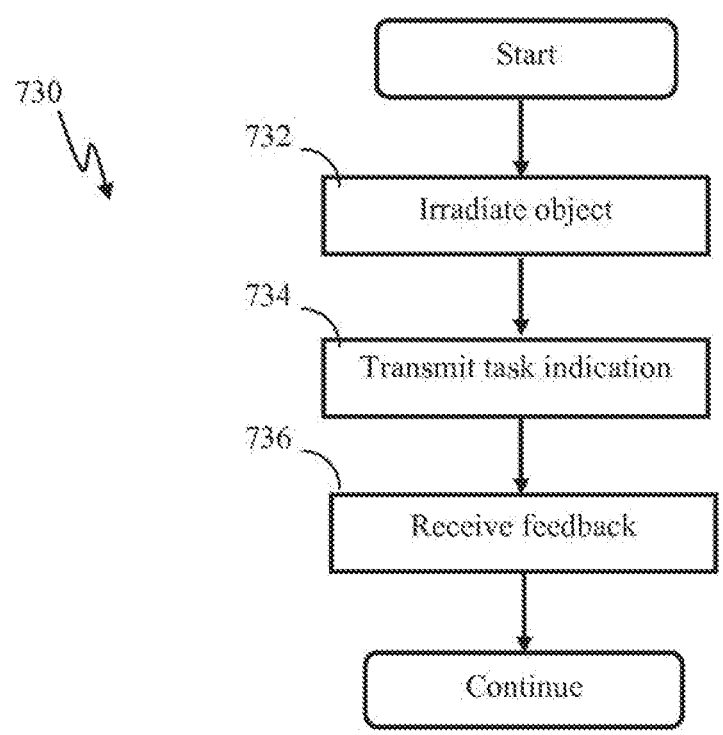
FIG. 7C is a logical flow diagram illustrating control of attention of the robotic apparatus of FIG. 4, in accordance with some implementations.

FIG. 7C illustrates one exemplary implementation of a method for controlling attention of the robotic apparatus (e.g., the apparatus 110 of FIG. 1 and/or inspection robot 410 of FIG. 4). The method contemplates the use of an external agent for controlling attention of the robot, operable in an environment comprising one or more objects of interest (e.g., a portion of airframe, a race track, and/or other objects).

At step 732, an external agent may irradiate the object of interest (e.g., the area 404 of the aircraft wing). In some implementations, the agent may utilize a spot light 206 of FIG. 2 emitting a beam of visible, infrared, ultra violet, and/or other wavelengths of light. In some implementations, the agent may utilize a radio frequency (RF) transmitter. In some implementations, the agent may utilize a sound transmitter to insonify an object underwater when controlling an underwater robotic device. The irradiating of the object may serve as an indication to the robotic device of the area (e.g., the footprint 404) that may require its attention. As illustrated in FIG. 4, the beam footprint 404 may cover a portion of the area of interest 414. The robotic device may comprise sufficient built-in and/or learned intelligence in order to be able to explore the surrounding indicated by the agent.

At step 734, the agent may further communicate to the robotic device an indication of a task to be performed that may be associated with the area/object of interest. In one or more implementations, the task indication may be communicated using the device used for irradiating the object (e.g., the spot light 206 comprising one or more buttons 204). Depending on the type of the robotic device (e.g., race bot, inspection robot, core drilling robot, etc., and/or the object (e.g., physically accessible or a remote object), various tasks may be performed, such as, for example, taking an image of the object, obtaining a physical sample, approaching the object, etc. In order to differentiate between various tasks, the task indication of step 734 may comprise task ID (e.g., single click, double click, etc.). Various task encoding methodologies exist in the arts such as pulse width modulation, phase, frequency, amplitude modulation, and/or other methodologies.

At step 736, feedback may be received by the agent from the robotic device. In some implementations, the feedback may inform the agent that the robot has commenced task execution and/or has completed the task. If the robot is unable to execute the task due to a variety of reasons such as, unavailable resource (e.g., a low battery, and/or the selected region is beyond the sensor range, and/or full sample compartment and/or memory) and/or an obstacle in its path, the feedback may comprise a flag indicating that the task cannot be completed.

The failure flag may be returned when the robotic device is unable to interpret the task notification, due to, for example, having an incompatible and/or outdated configuration (e.g., an inspection only robot receiving a task code to obtain core sample).

Figure 8:
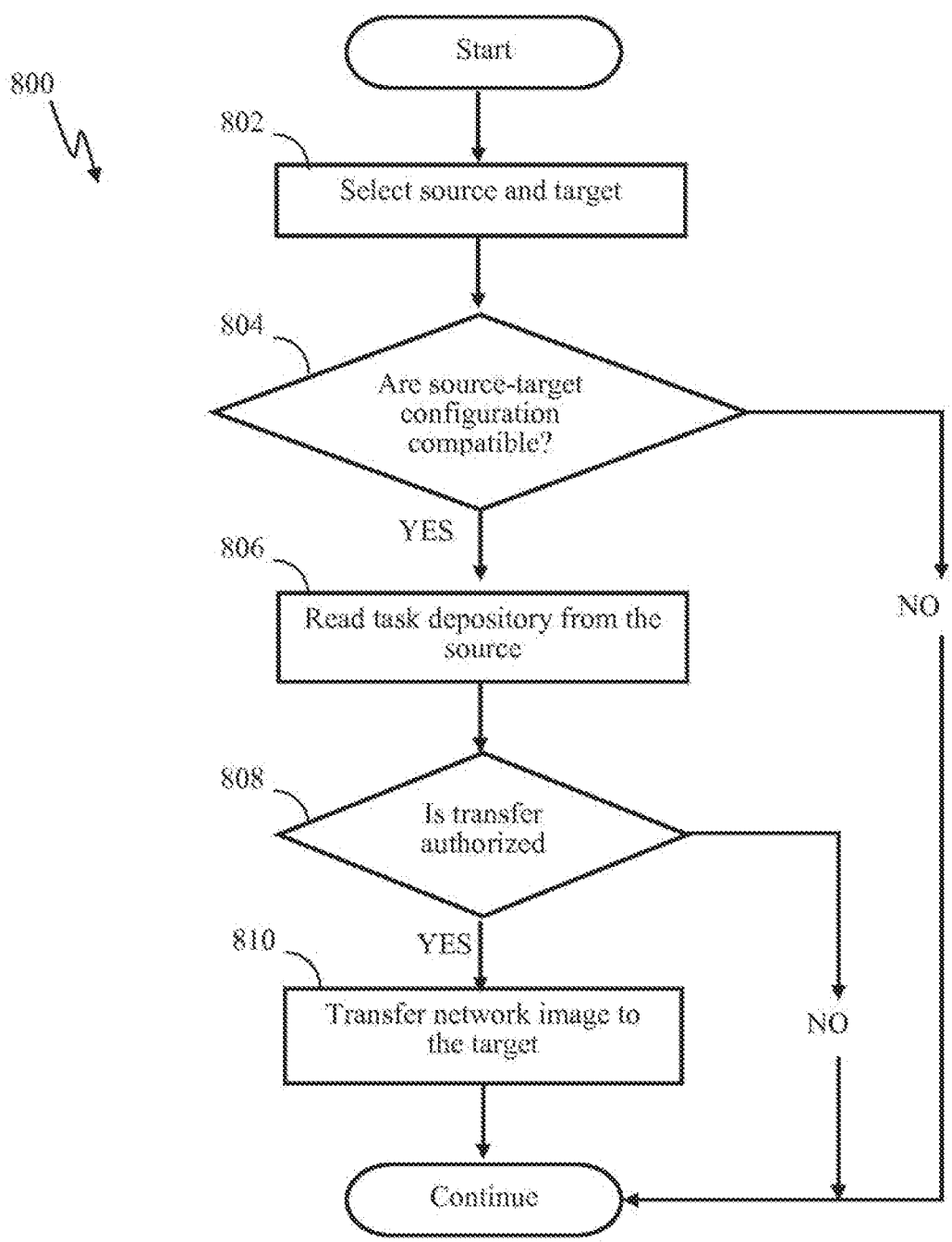
FIG. 8 is a logical flow diagram illustrating transfer of context learned by the robotic apparatus of FIG. 4, in accordance with some implementations.

Referring now to FIG. 8, one exemplary implementation of a method for transferring context learned by, for example, the robotic apparatus of FIG. 4 is shown and described.

At step 802, a source and destination may be selected. In some implementations, the source and destination may each comprise the robotic device 410 of FIG. 4. In one or more implementations, either the source or the destination may comprise an external depository described in detail with respect to FIGS. 9A-9D, below.

When the source and the destination comprise the robotic device, a configuration compatibility check is performed at step 804. The check of step 804 may comprise hardware (e.g., memory size, sensor suite) and/or software (e.g., driver version, network description language version) compatibility. In some implementations, the network description may comprise high-level neuromorphic description framework described in detail in U.S. patent application Ser. No. 13/385,938, filed Mar. 15, 2012 and entitled "TAG-BASED APPARATUS AND METHODS FOR NEURAL NETWORKS," now U.S. Pat. No. 8,712,939, the contents of which are incorporated herein by reference in their entireties.

At step 806, the network image, comprising one or more learned context, may be read from the target.

At step 808, the authorization of the transfer may be performed. In some implementations, the authorization may comprise image verification and/or validation in order to determine, for example, if the image is provided by a legitimate source; the target device is authorized and/or eligible to receive the image; and/or perform other certification tasks.

Upon successful authorization, the image may be downloaded to the target device at step 810.

As described supra, the present disclosure envisages the user ability to share content related to the training of such robotic devices. In various implementations, a user may extract the state of a neural network (or other useful training-related information) directly from the device. The artificial mind and its traits may be copied, stored, and later retrieved.

Figure 9A:
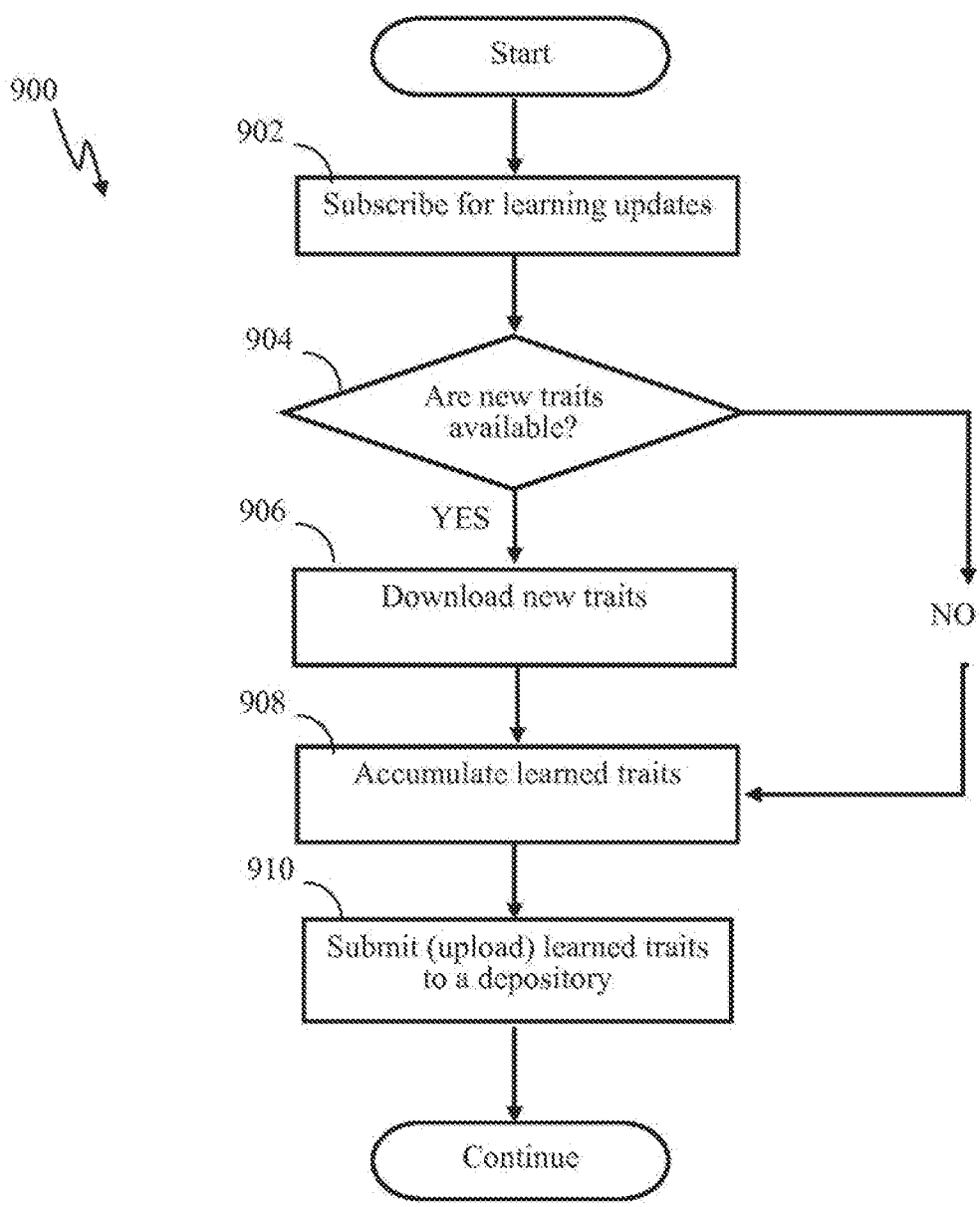
FIG. 9A is a logical flow diagram illustrating generalized method for life cycle management of learning network of a robotic apparatus, in accordance with some implementations.

FIG. 9A illustrates a generalized method for life cycle management of learning network of a robotic apparatus, in accordance with some implementations.

At step 902 of method 900, a user of the robotic apparatus (e.g., the race bot 110 of FIG. 1) may subscribe to network updates. In some implementations, the subscription may comprise feature download or upload only. In some implementations, the subscription may comprise both the download and upload options. In one or more implementations, the subscription may provide user with subscription credit (monetary and/or points) for uploading new learned traits (e.g., the context described with respect to step 726 supra) into the depository.

At step 904, the user may train the robotic apparatus to learn task association (e.g., context) in accordance with any of the methodologies described above with respect to FIGS. 1-6.

At step 906, the user may upload learned traits into the shared depository (e.g., the cloud store 1206 of FIG. 12, described infra).

At step 908, the user may check if network image(s) comprising new traits are available at the depository.

When available, the user may download new traits at step 910.

Figure 9B:
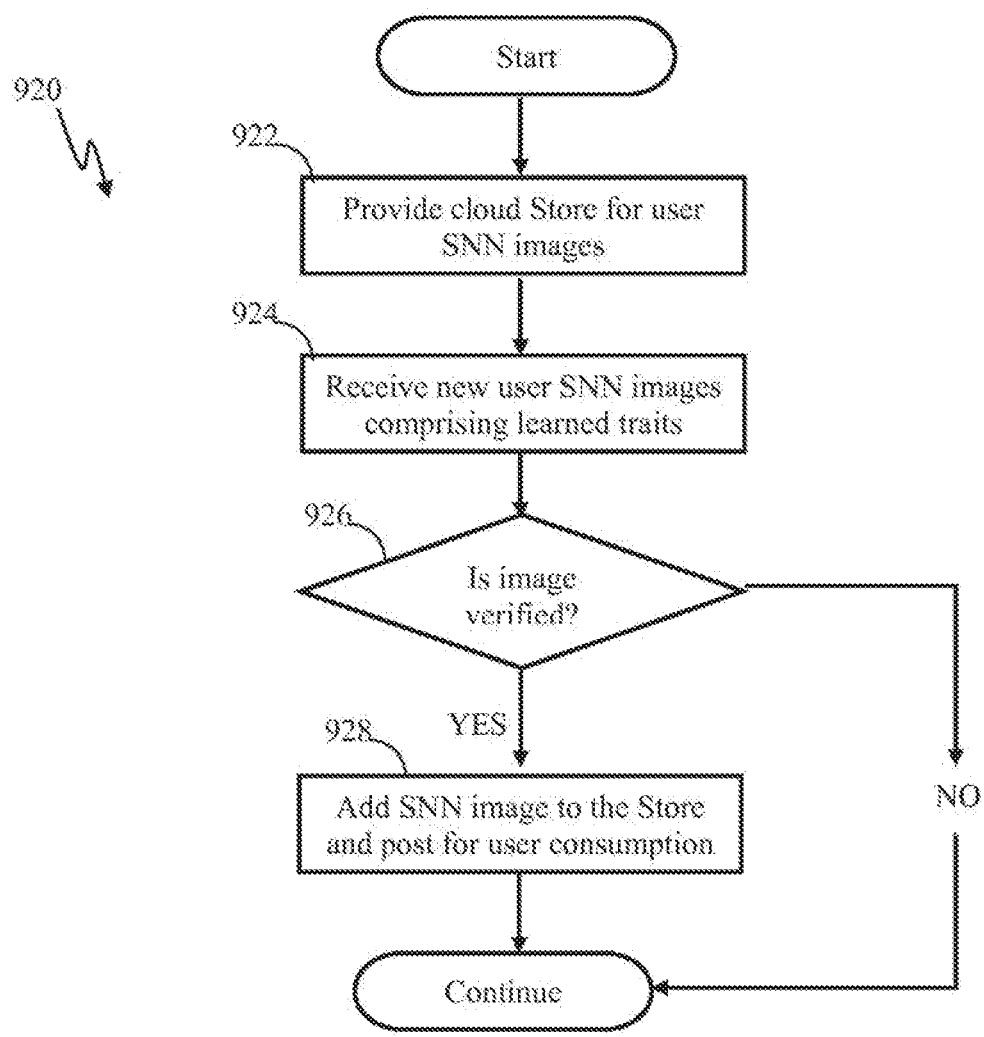
FIG. 9B is a logical flow diagram illustrating generalized method for cloud store of learned traits life cycle management, in accordance with some implementations.
Figure 9C:
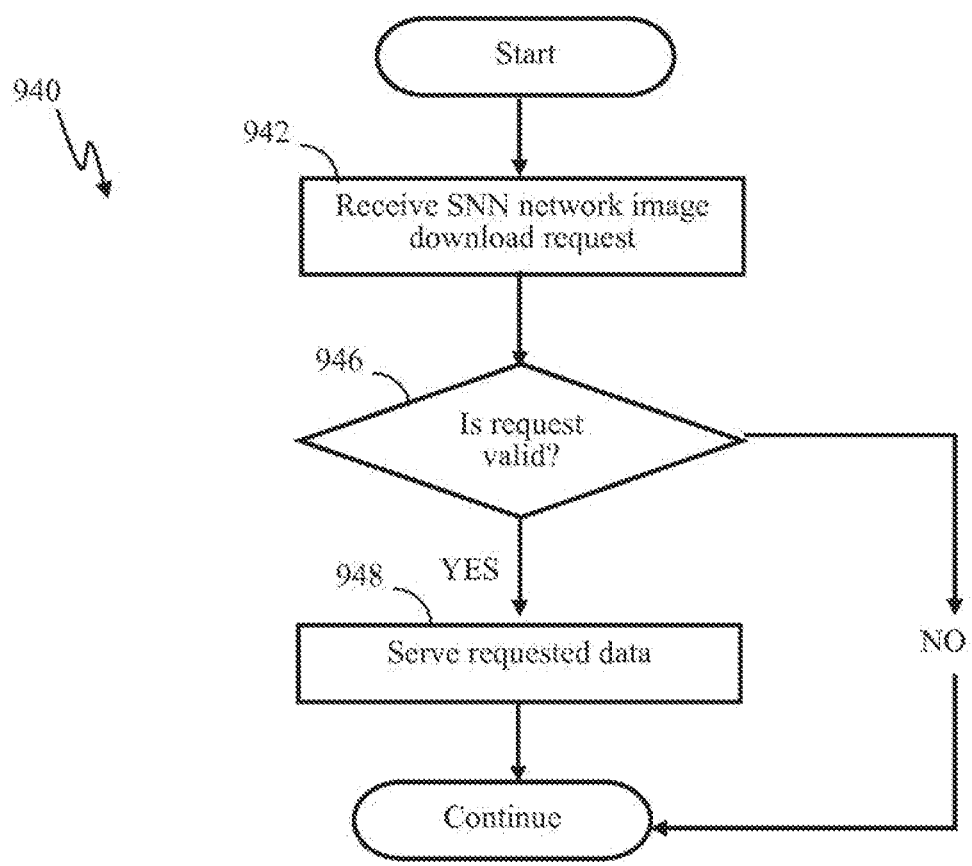
FIG. 9C is a logical flow diagram illustrating provision of learned traits by the cloud store, in accordance with some implementations.

FIGS. 9B-9C illustrate generalized methods of cloud store operation configured to enable users of robotic devices to share learned traits, in accordance with one or more implementations.

At step 922 of method 920 of FIG. 9B, users are provided with access to the cloud store (e.g., the depository 1206 of FIG. 12).

In some implementations, access may comprise a storefront being provided as a user interface to the cloud. From the storefront, users may access purchasable content (e.g. brain images, upgrades, alternate firmware packages). Purchasable content may allow users to conveniently obtain quality content to enhance their user experience. The quality may be controlled under any number of different mechanisms, such as peer review, user rating systems, functionality testing before the image is 'uploadable' and/or made accessible, and/or other mechanisms. In some cases, users may prefer different starting points in training. Some users may generally prefer to begin with a clean slate, or to use only their own brain images as starting points. Users may generally prefer not to have to redo training that has already been (properly or suitably) performed. Users may appreciate having easy access to quality-controlled purchasable content.

A subscription model may be used. In various implementations, a user gains access to content based on a periodic payment to the administrator of the networked service. A hybrid model may be used. An initial/periodic subscription fee may allow access to general material. Premium content may require a specific payment.

Other users that develop skill in training or those that develop popular brain images may wish to monetize their creations. The exemplary storefront implementation provides a platform for such enterprise. Operators of storefronts may desire to encourage such enterprise both for revenue generation and for enhanced user experience. The storefront operator may institute competitions with prizes for the most popular brain images, modifications, and/or media. Users may be motivated to create higher quality content. The operator may (in or in lieu of a contest) instate a system of revenue and/or profit sharing for purchasable content. Hobbyists and casual developers may see a reasonable return on their efforts. Such a system may attract professional developers. Users as a whole may benefit from a wider array of content offerings from more skilled developers.

At step 924, a network image file (comprising, inter alia, new and/or improved learned traits) may be received from a user.

At step 926 the image may be verified for compatibility, consistency and/or presence of undesirable and/or malicious content (e.g., advertising and/or viruses).

When the image is verified, the new traits may be added to the Store depository at step 928.

FIG. 9C illustrates provision of learned traits by the cloud store, in accordance with some implementations.

At step 942 of method 940 of FIG. 9C, the Store may receive a user request to for an SNN image download. As described above, the request may be based on a purchase, peer-to-peer share, and or subscription-based service agreement with users of robotic devices.

At step 946, the user request may be validated to determine user authenticity and/or eligibility to obtain the network image. By way of illustration, a fee based subscription may allow for a predetermined number of downloads (e.g., 3) in a time period, so that download requests in excess of the allotted amount may be rejected.

When a request is valid, at step 946 the requested data may be provided to the user for download.

Figure 9D:
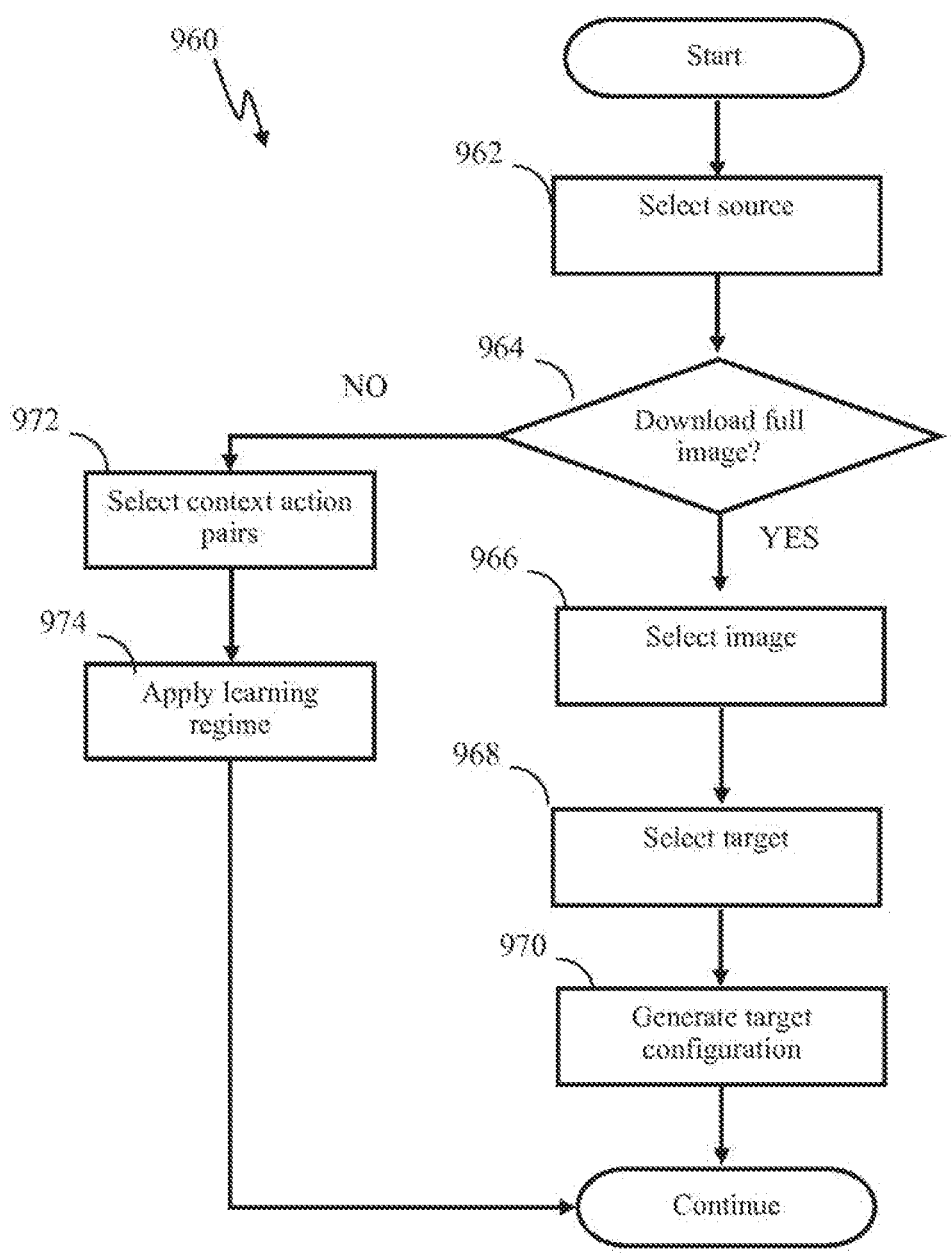
FIG. 9D is a logical flow diagram illustrating download of network image from cloud store, in accordance with some implementations.

Referring now to FIG. 9D, exemplary uses of the network life cycle methodology according to the disclosure are described. In some implementations, the method of FIG. 9D may be used, for example, for operating the robotic apparatus 410 of FIG. 4. The method FIG. 9D may be implemented for example in a robotic device configured for processing sensory data as described in FIG. 10, infra, thereby advantageously aiding, inter alia, signal compression, and/or object recognition when processing visual sensory input.

Returning now to FIG. 9D, at step 962 of the method 960, a source of the new network configuration may be selected. When the source comprises another robotic device(s), a connection to the device (via, e.g., USB, or a wireless link) may be established. In some implementations, two (or more) robotic devices may be linked via a user computing device (e.g., a desktop, laptop, a smartphone, a tablet, and/or other computing device).

When the source comprises a cloud depository, a session with the Store may be established.

At step 964, a check may be performed as to whether the download comprises a full image download or an addition training samples of context action pairs. By way of illustration, a user with a robotic device comprising a network partitioned into a visual processing network block and a motor control network block, may desire to add new vision processing functionality, responsive, for example, to a camera upgrade, while leaving the motor functionality unaffected. The users may desire to add selected traits (e.g., ability of the race bot 310 of FIG. 1 to navigate sharp turns on the track 302 of FIG. 3 at higher speeds), thereby preferring partial network updates.

When the full image is to be downloaded, the method 960 may proceed to step 966, where the image type is selected. In some implementations, the image may correspond to the robotic brain image from another robotic device that has been previously trained, described in detail with respect to FIG. 4, supra, while in some implementations, the image may correspond to the network merge described in detail in U.S. patent application Ser. No. 13/830,398, entitled "NEURAL NETWORK LEARNING AND COLLABORATION APPARATUS AND METHODS," now U.S. Pat. No. 9,208,432, incorporated supra.

When a partial image (comprising for example, context action pairs for a particular cognitive channel) is to be downloaded, the method 960 may proceed to step 972, where the individual traits and/or network blocks may be selected for download. Traits from multiple sources (multiple parents) may be selected and combined into a single image download via a network merge described in detail in detail in U.S. patent application Ser. No. 13/830,398, entitled "NEURAL NETWORK LEARNING AND COLLABORATION APPARATUS AND METHODS," now U.S. Pat. No. 9,208,432, incorporated supra.

At step 974, the download image may be assembled. In some implementations, the assembled image may be configured in accordance with the architecture of the target device, which may be selected at step 968.

At step 968, the target network (the offspring) may be selected. In one or more implementations, the target may comprise the off-spring (e.g., the network of the device being updated/transformed). In some implementations, the target may comprise a network image configured to be stored within a cloud server, and/or downloaded to one or more devices (e.g., the devices 1210 in FIG. 12).

At step 970, the target network configuration may be generated. In one or more implementations, the target configuration may comprise network weights downloaded into the target robotic device. In some implementations, the target configuration may comprise network weights vector stored within the cloud server and available for subsequent downloads to one or more robotic devices (e.g., 1210 of FIG. 12).

Figure 10:
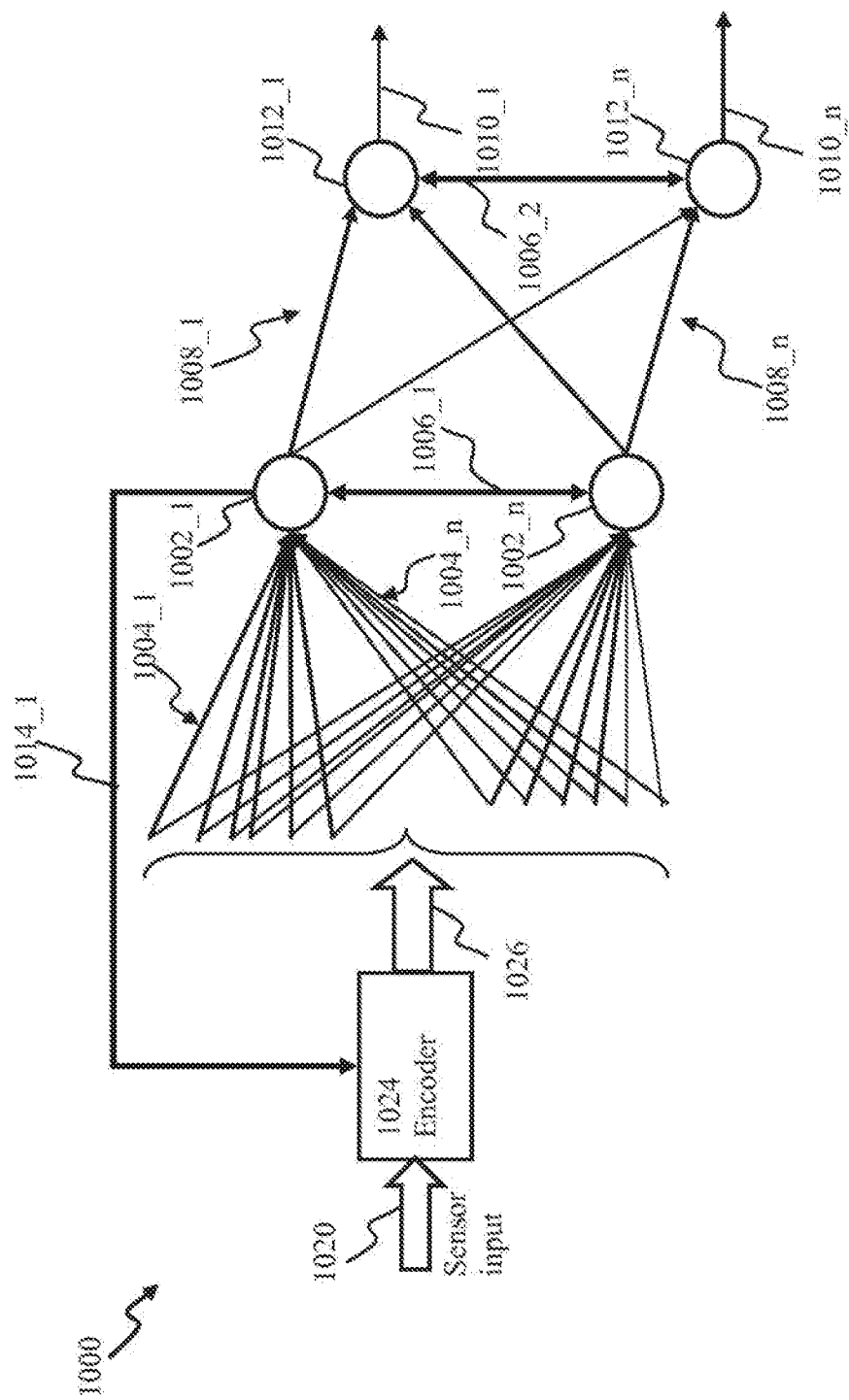
FIG. 10 is a block diagram illustrating sensory processing apparatus configured to implement detection of salient features, in accordance with some implementations.

One spiking neuron network apparatus for processing of sensory information (e.g., visual, audio, somatosensory) useful in an autonomous robotic device, is shown in FIG. 10. The illustrated processing apparatus 1000 may comprise an input interface configured to receive an input sensory signal 1020. In some implementations, this sensory input comprises electromagnetic waves (e.g., visible light, IR, UV, and/or other electromagnetic wages) entering an imaging sensor array (comprising RGCs, a charge coupled device (CCD), or an active-pixel sensor (APS)). The input signal in this case is a sequence of images (image frames) received from a CCD camera via a receiver apparatus, or downloaded from a file. The image may be a two-dimensional matrix of RGB values refreshed at a 24 Hz frame rate. It will be appreciated by those skilled in the art that the above image parameters are merely exemplary, and many other image representations (e.g., bitmap, CMYK, grayscale, and/or other image representations) and/or frame rates are equally useful with the present invention.

The apparatus 1000 may comprise an encoder 1024 configured to transform (encodes) the input signal into an encoded signal 1026. In some implementations, the encoded signal comprises a plurality of pulses (also referred to as a group of pulses) configured to model neuron behavior. The encoded signal 1026 may be communicated from the encoder 1024 via multiple connections (also referred to as transmission channels, communication channels, or synaptic connections) 1004 to one or more neuronal nodes (also referred to as the detectors) 1002.

In the implementation of FIG. 10, different detectors of the same hierarchical layer may be denoted by an "_n" designator, such that e.g., the designator 1002_1 denotes the first detector of the layer 1002. Although only two detectors (1002_1, 1002_n) are shown in the implementation of FIG. 10 for clarity, it is appreciated that the encoder can be coupled to any number of detector nodes that is compatible with the detection apparatus hardware and software limitations. A single detector node may be coupled to any practical number of encoders.

In some implementations, individual ones of the detectors 1002_1, 1002_n may contain logic (which may be implemented as a software code, hardware logic, or a combination of thereof) configured to recognize a predetermined pattern of pulses in the encoded signal 1004, using for example any of the mechanisms described in U.S. patent application Ser. No. 12/869,573, filed Aug. 26, 2010 and entitled "SYSTEMS AND METHODS FOR INVARIANT PULSE LATENCY CODING," now U.S. Pat. No. 8,315,305, U.S. patent application Ser. No. 12/869,583, filed Aug. 26, 2010, entitled "INVARIANT PULSE LATENCY CODING SYSTEMS AND METHODS," now U.S. Pat. No. 8,467,623, U.S. patent application Ser. No. 13/117,048, filed May 26, 2011 and entitled "APPARATUS AND METHODS FOR POLYCHRONOUS ENCODING AND MULTIPLEXING IN NEURONAL PROSTHETIC DEVICES," now U.S. Pat. No. 9,311,593, U.S. patent application Ser. No. 13/152,084, filed Jun. 2, 2011, entitled "APPARATUS AND METHODS FOR PULSE-CODE INVARIANT OBJECT RECOGNITION," now U.S. Pat. No. 9,405,975, each incorporated herein by reference in its entirety, to produce post-synaptic detection signals transmitted over communication channels 1008. In FIG. 10, the designators 1008_1, 1008_n denote output of the detectors 1002_1, 1002_n, respectively.

In some implementations, the detection signals are delivered to a next layer of the detectors 1012 (comprising detectors 1012_1, 1012_m, 1012_k) for recognition of complex object features and objects, similar to the exemplary implementation described in commonly owned and co-pending U.S. patent application Ser. No. 13/152,084, filed Jun. 2, 2011, entitled "APPARATUS AND METHODS FOR PULSE-CODE INVARIANT OBJECT RECOGNITION", now U.S. Pat. No. 9,405,975, incorporated supra. In this implementation, individual subsequent layers of detectors may be configured to receive signals from the previous detector layer, and/or to detect more complex features and objects (as compared to the features detected by the preceding detector layer). For example, a bank of edge detectors may be followed by a bank of bar detectors, followed by a bank of corner detectors to enable alphabet recognition.

Individual ones of the detectors 1002 may output detection (e.g., post-synaptic) signals on communication channels 1008_1, 1008_n (with appropriate latency) that may propagate with different conduction delays to the detectors 1012. The detector cascade of the implementation of FIG. 10 may contain any practical number of detector nodes and detector banks determined, inter alia, by the software/hardware resources of the detection apparatus and complexity of the objects being detected.

The sensory processing apparatus implementation illustrated in FIG. 10 may comprise lateral connections 1006. In some implementations, the connections 1006 may be configured to communicate post-synaptic activity indications between neighboring neurons of the same hierarchy level, as illustrated by the connection 1006_1 in FIG. 10.

In some implementations, the apparatus 1000 may comprise feedback connections 1014, configured to communicate context information from detectors within one hierarchy layer to previous layers, as illustrated by the feedback connections 1014_1 in FIG. 10. In some implementations, the feedback connection 1014_2 may be configured to provide feedback to the encoder 1024 thereby facilitating sensory input encoding, as described in detail in commonly owned and co-pending U.S. patent application Ser. No. 13/152,084, filed Jun. 2, 2011, entitled "APPARATUS AND METHODS FOR PULSE-CODE INVARIANT OBJECT RECOGNITION," now U.S. Pat. No. 9,405,975, incorporated supra.

Some implementations of the computerized neuromorphic processing system, for operating a computerized spiking network (and implementing the exemplary sensory processing methodology described supra), is illustrated in FIG. 11A.

Some implementations of the computerized neuromorphic processing system, for use with salient feature detection apparatus described supra, is illustrated in FIG. 11A. The computerized system 1100 of FIG. 11A may comprise an input device 1110, such as, for example, an image sensor and/or digital image interface. The input interface 1110 may be coupled to the processing block (e.g., a single or multi-processor block) via the input communication interface 1114. In some implementations, the interface 1114 may comprise a wireless interface (cellular wireless, Wi-Fi, Bluetooth, and/or other wireless interface) that enables data transfer to the processor 1102 from remote I/O interface 1100. One such implementation may comprise a central processing apparatus coupled to one or more remote camera devices comprising salient feature detection apparatus of the disclosure.

The system 1100 further may comprise a random access memory (RAM) 1108 configured to store neuronal states and connection parameters and to facilitate synaptic updates. In some implementations, synaptic updates are performed according to the description provided in, for example, in U.S. patent application Ser. No. 13/239,255 filed Sep. 21, 2011, entitled "APPARATUS AND METHODS FOR SYNAPTIC UPDATE IN A PULSE-CODED NETWORK," now U.S. Pat. No. 9,147,156, incorporated by reference in its entirety.

In some implementations, the memory 1108 may be coupled to the processor 1102 via a direct connection (memory bus) 1116, and/or via a high-speed processor bus 1112). In some implementations, the memory 1108 may be embodied within the processor block 1102.

The system 1100 may further comprise a nonvolatile storage device 1106, comprising, inter alia, computer readable instructions configured to implement various aspects of spiking neuronal network operation (e.g., sensory input encoding, connection plasticity, operation model of neurons, and/or other aspects). in one or more implementations, the nonvolatile storage 1106 may be used to store state information of the neurons and connections when, for example, saving/loading network state snapshot, or implementing context switching (e.g., saving current network configuration, which may comprise, inter alia, connection weights and update rules, neuronal states and learning rules, and/or other components) for later use and loading previously stored network configuration.

In some implementations, the computerized apparatus 1100 may be coupled to one or more external processing/storage/input devices via an I/O interface 1120, such as a computer I/O bus (PCI-E), wired (e.g., Ethernet) and/or wireless (e.g., Wi-Fi) network connection.

It will be appreciated by those skilled in the arts that various processing devices may be used with computerized system 1100, including but not limited to, a single core/multicore CPU, DSP, FPGA, GPU, ASIC, combinations thereof, and/or other processors. Various user input/output interfaces are similarly applicable to implementations of the invention including, for example, an LCD/LED monitor, touch-screen input and display device, speech input device, stylus, light pen, trackball, end the likes.

Figure 11B:
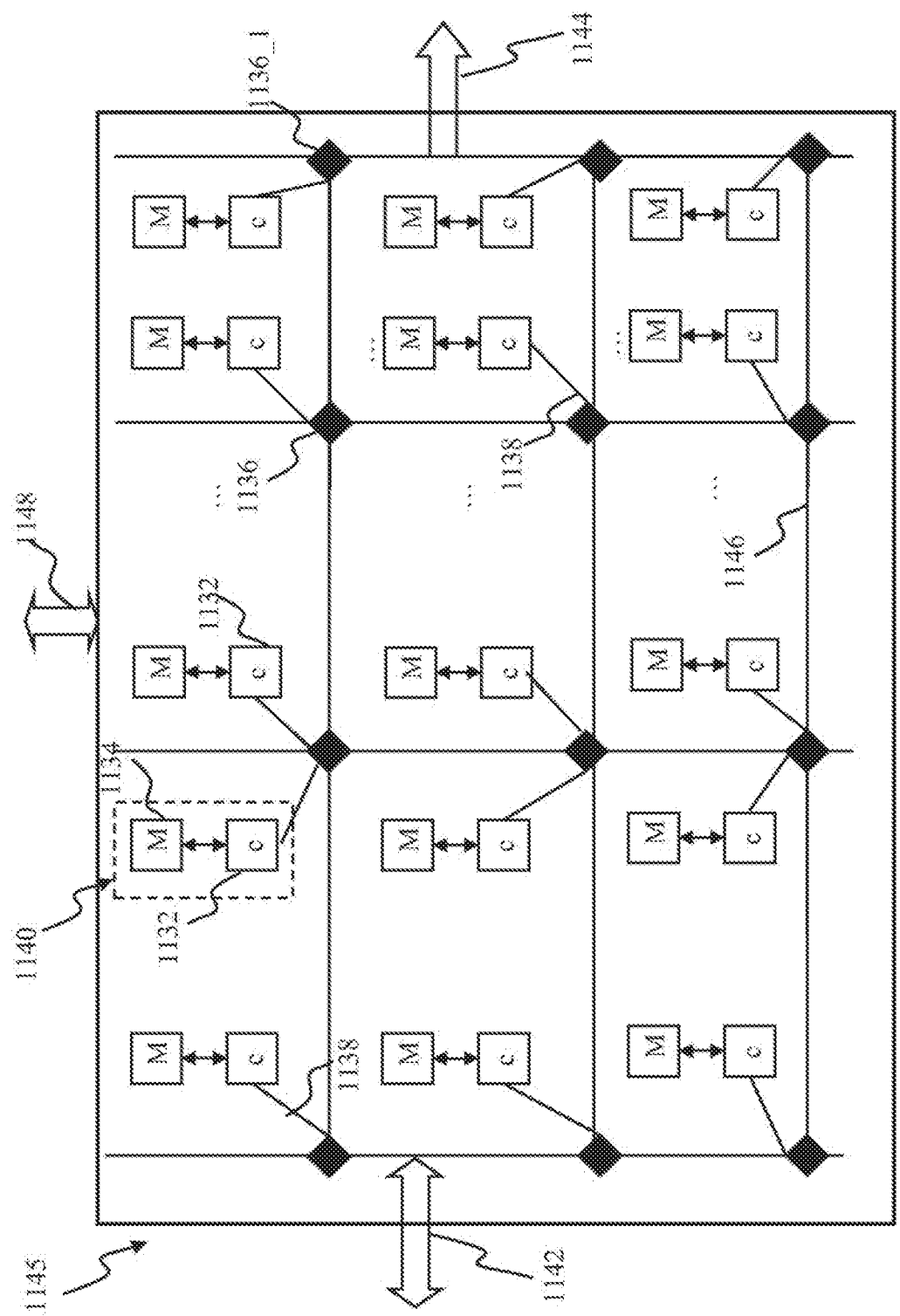
FIG. 11B is a block diagram illustrating a grid-type computerized system useful with the attention mapping methodology of the disclosure, according to some implementations.

FIG. 11B, illustrates some implementations of neuromorphic computerized system configured for use with salient feature detection apparatus described supra. The neuromorphic processing system 1130 of FIG. 11B may comprise a plurality of processing blocks (micro-blocks) 1140, where each micro core may comprise logic block 1132 and memory block 1134, denoted by 'L' and 'M' rectangles, respectively, in FIG. 11B. The logic block 1132 may be configured to implement various aspects of salient feature detection, such as the latency encoding described in U.S. patent application Ser. No. 12/869,573, entitled "SYSTEMS AND METHODS FOR INVARIANT PULSE LATENCY CODING," now U.S. Pat. No. 8,315,305, filed Aug. 26, 2010, incorporated supra, neuron unit dynamic model, detector nodes 1022 if FIG. 10A, and/or inhibitory nodes 1029 of FIG. 10A. The logic block may implement connection updates (e.g., the connections 1014, 1026 in FIG. 10A) and/or other tasks relevant to network operation. In some implementations, the update rules may comprise rules spike time dependent plasticity (STDP) updates. The memory block 1024 may be configured to store, inter alia, neuronal state variables and connection parameters (e.g., weights, delays, I/O mapping) of connections 1138.

One or more micro-blocks 1140 may be interconnected via connections 1138 and routers 1136. In one or more implementations (not shown), the router 1136 may be embodied within the micro-block 1140. As it is appreciated by those skilled in the arts, the connection layout in FIG. 11B is exemplary and many other connection implementations (e.g., one to all, all to all, etc.) are compatible with the disclosure.

The neuromorphic apparatus 1130 may be configured to receive input (e.g., visual input) via the interface 1142. In one or more implementations, applicable for example to interfacing with a pixel array, the apparatus 1130 may be configured to provide feedback information via the interface 1142 to facilitate encoding of the input signal.

The neuromorphic apparatus 1130 may be configured to provide output (e.g., an indication of recognized object or a feature, or a motor command, e.g., to zoom/pan the image array) via the interface 1144.

The apparatus 1130, in one or more implementations, may interface to external fast response memory (e.g., RAM) via high bandwidth memory interface 1148, thereby enabling storage of intermediate network operational parameters (e.g., spike timing, etc.). In one or more implementations, the apparatus 1130 may also interface to external slower memory (e.g., flash, or magnetic (hard drive)) via lower bandwidth memory interface 1146, in order to facilitate program loading, operational mode changes, and retargeting, where network node and connection information for a current task may be saved for future use and flushed, and previously stored network configuration may be loaded in its place, as described for example in co-pending and co-owned U.S. patent application Ser. No. 13/487,576 entitled "DYNAMICALLY RECONFIGURABLE STOCHASTIC LEARNING APPARATUS AND METHODS", filed Jun. 4, 2012, now U.S. Pat. No. 9,015,092, incorporated supra.

Figure 11C:
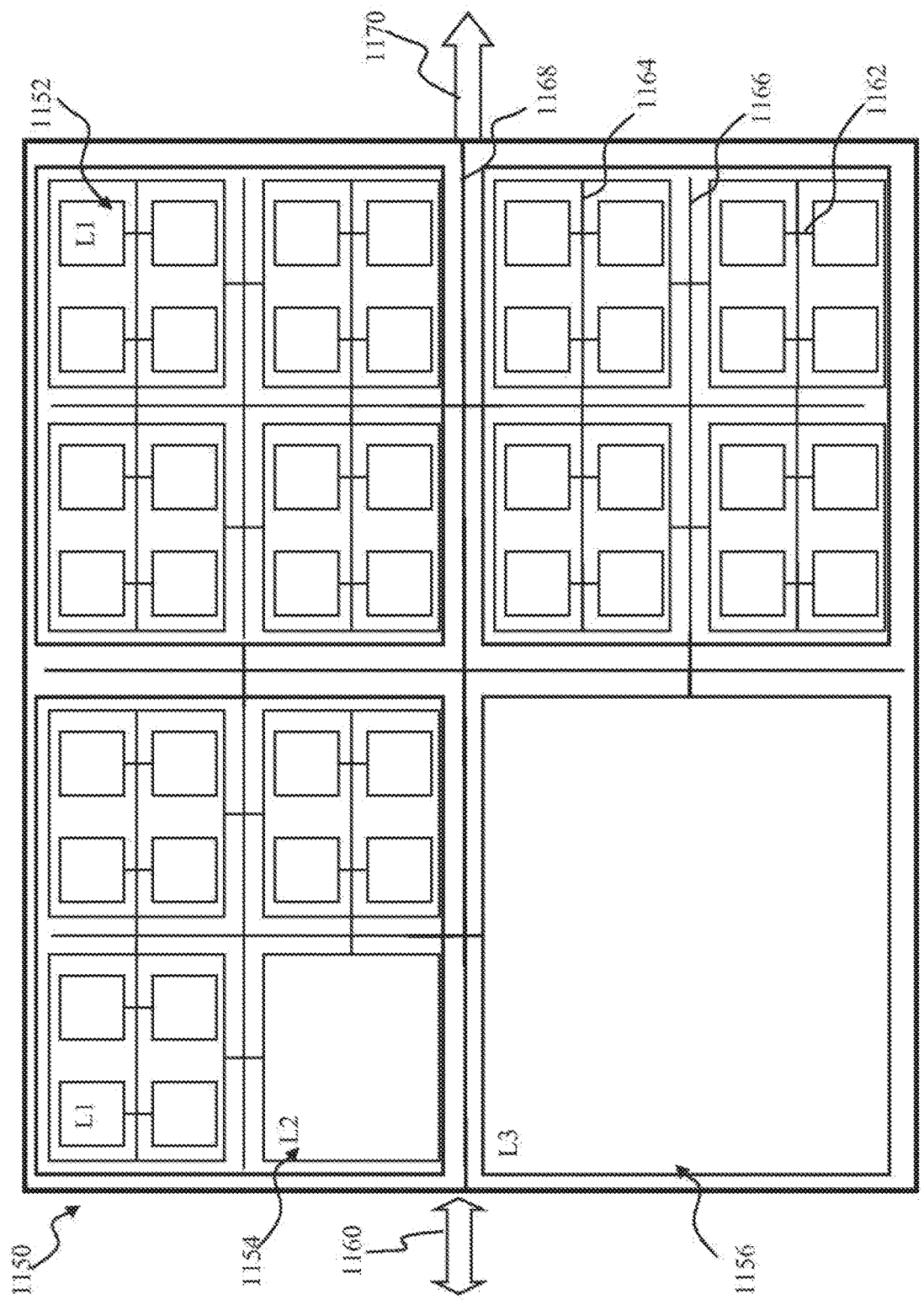
FIG. 11C is a block diagram illustrating a hierarchical computerized system architecture useful with the attention mapping methodology of the disclosure, according to some implementations.

FIG. 11C illustrates some implementations of cell-based hierarchical neuromorphic system architecture configured to implement salient feature detection. The neuromorphic system 1150 of FIG. 11C may comprise a hierarchy of processing blocks (cells block) 1140. In some implementations, the lowest level L1 cell 1152 of the apparatus 1150 may comprise logic and memory, and may be configured similar to the micro block 1140 of the apparatus shown in FIG. 11B, supra. A number of cell blocks 1052 may be arranges in a cluster 1154 and communicate with one another via local interconnects 1162, 1164. Individual ones of such clusters may form higher level cell, e.g., cell denoted L2 in FIG. 11C. Similarly several L2 level clusters may communicate with one another via a second level interconnect 1166 and form a super-cluster L3, denoted as 1156 in FIG. 11C. The super-clusters 1156 may communicate via a third level interconnect 1168 and may form a higher-level cluster, and so on. It will be appreciated by those skilled in the arts that hierarchical structure of the apparatus 1150, comprising four cells-per-level, shown in FIG. 11C represents one exemplary implementation and other implementations may comprise more or fewer cells/level and/or fewer or more levels.

Different cell levels (e.g., L1, L2, L3) of the apparatus 1150 may be configured to perform functionality various levels of complexity. In some implementations, different L1 cells may process in parallel different portions of the visual input (e.g., encode different frame macro-blocks), with the L2, L3 cells performing progressively higher level functionality (e.g., edge detection, object detection). Different L2, L3, cells may perform different aspects of operating, for example, a robot, with one or more L2/L3 cells processing visual data from a camera, and other L2/L3 cells operating motor control block for implementing lens motion what tracking an object or performing lens stabilization functions.

The neuromorphic apparatus 1150 may receive visual input (e.g., the input 1002 in FIG. 10) via the interface 1160. In one or more implementations, applicable for example to interfacing with a latency encoder and/or an image array, the apparatus 1150 may provide feedback information via the interface 1160 to facilitate encoding of the input signal.

The neuromorphic apparatus 1150 may provide output (e.g., an indication of recognized object or a feature, or a motor command, e.g., to zoom/pan the image array) via the interface 1170. In some implementations, the apparatus 1150 may perform all of the I/O functionality using single I/O block (e.g., the I/O 1160 of FIG. 11C).

The apparatus 1150, in one or more implementations, may interface to external fast response memory (e.g., RAM) via high bandwidth memory interface (not shown), thereby enabling storage of intermediate network operational parameters (e.g., spike timing, etc.). The apparatus 1150 may also interface to a larger external memory (e.g., flash, or magnetic (hard drive)) via a lower bandwidth memory interface (not shown), in order to facilitate program loading, operational mode changes, and retargeting, where network node and connection information for a current task may be saved for future use and flushed, and previously stored network configuration may be loaded in its place, as described for example in co-pending and co-owned U.S. patent application Ser. No. 13/487,576, entitled "DYNAMICALLY RECONFIGURABLE STOCHASTIC LEARNING APPARATUS AND METHODS," now U.S. Pat. No. 9,015,092, incorporated supra.

Methodology described herein may advantageously allow for real-time control of the robots attention by an external smart agent. The external agent may be better equipped for disregarding distractors, as well as rapidly changing strategies when the circumstances of the environment demand a new cost function (e.g. a switch in the task at hand.) The system may provide means to train up the robot's attention system. In other words, it learns that what it should (automatically) attend to for a particular context, is what the external operator has guided it to in the past.

Exemplary implementations may be useful with a variety of devices including without limitation autonomous and robotic apparatus, and other electromechanical devices requiring attention guidance functionality. Examples of such robotic devises may include one or more of manufacturing robots (e.g., automotive), military, medical (e.g. processing of microscopy, x-ray, ultrasonography, tomography), and/or other robots. Examples of autonomous vehicles may include one or more of rovers, unmanned air vehicles, underwater vehicles, smart appliances (e.g. ROOMBA®), inspection and/or surveillance robots, and/or other vehicles.

Implementations of the principles of the disclosure may be used for entertainment, such as one or more of multi-player games, racing, tag, fetch, personal sports coaching, chasing off crop scavengers, cleaning, dusting, inspection of vehicles and goods, cooking, object retrieval, tidying domestic clutter, removal of defective parts, replacement of worn parts, construction, roof repair, street repair, automotive inspection, automotive maintenance, mechanical debauchery, garden maintenance, fertilizer distribution, weeding, painting, litter removal, food delivery, drink delivery, table wiping, party tricks, and/or other applications.

Implementations of the principles of the disclosure may be applicable to training coordinated operations of automated devices. For example, in applications such as unexploded ordinance/improvised explosive device location and removal, a coordinated search pattern between multiple autonomous learning devices leads to more efficient area coverage. Learning devices may offer the flexibility to handle wider (and dynamic) variety of explosive device encounters. Such learning devices may be trained to identify targets (e.g. enemy vehicles) and deliver similar explosives.

It will be recognized that while certain aspects of the invention are described in terms of a specific sequence of steps of a method, these descriptions are only illustrative of the broader methods of the invention, and may be modified as required by the particular application. Certain steps may be rendered unnecessary or optional under certain circumstances. Additionally, certain steps or functionality may be added to the disclosed implementations, or the order of performance of two or more steps permuted. All such variations are considered to be encompassed within the invention disclosed and claimed herein.

While the above detailed description has shown, described, and pointed out novel features of the invention as applied to various implementations, it will be understood that various omissions, substitutions, and changes in the form and details of the device or process illustrated may be made by those skilled in the art without departing from the invention. The foregoing description is of the best mode presently contemplated of carrying out the invention. This description is in no way meant to be limiting, but rather should be taken as illustrative of the general principles of the invention. The scope of the invention should be determined with reference to the claims.

What is claimed is:

1. An automated control system comprising:
   a robotic apparatus comprising:
   a sensor,
   a transmitter, and
   a receiver;
   an input device comprising:
   an input/output interface,
   an interface comprising a wireless interface in communication with the robotic apparatus, wherein the interface is configured to communicate with a display device through the input/output interface,
   a transmitter, and
   a receiver;
   an attention-trigger apparatus; and
   memory comprising:
   task association data including one or more tasks for execution by the robotic apparatus;
   wherein the sensor processes data within a visual field;
   wherein the input device in conjunction with the attention-trigger apparatus are configured to permit an operator to remotely select an object of interest from the visual field; and
   wherein a task is selected from the task association data and the robotic apparatus executes the task with respect to the object of interest from the visual field.

2. The automated control system of claim 1, wherein the robotic apparatus is configured to provide an acknowledgement feedback that a task selected from the task association data has been received, and wherein the attention-trigger apparatus is a flashlight.

3. The automated control system of claim 1, wherein the task is a command that the robotic apparatus follows the object of interest, and wherein the display device is part of the input device.

4. The automated control system of claim 1, wherein the sensor is a digital camera.

5. The automated control system of claim 1, comprising a tagging block that allows the operator to send a tag to the robotic apparatus related to another object within the visual field.

6. A method comprising:
   receiving an input signal from a sensor associated with a visual field of the robotic apparatus;
   selecting an object of interest within the visual field from the input signal;
   guiding attention of the robotic apparatus to the object of interest within the visual field;
   remotely operating the robotic apparatus;

selecting a task from task association data; and sending the task association data and information associated with the object of interest to the robotic apparatus so that the task is performed by the robotic apparatus regarding the object of interest, wherein the task performed by the robotic apparatus is to follow the object of interest.

7. The method of claim 6, comprising sending the task from an input device to the robotic apparatus.

8. The method of claim 6, comprising sending the task from a remote user device wirelessly to the robotic apparatus.

9. The method of claim 8, wherein a signal is transmitted from the robotic apparatus to the remote user device.

10. The method of claim 9, wherein the remote user device is a smartphone and the signal is an image.

11. The method of claim 7, wherein the object of interest is another robotic apparatus.

12. A method comprising:

receiving an input signal from a sensor associated with a robotic apparatus;

selecting a task from task association data;

selecting, using an attention-trigger apparatus, an object of interest;

remotely operating the robotic apparatus by instructing the robotic apparatus to perform an action related to the object of interest based upon the task selected; and switching, using the attention-trigger apparatus, from the object of interest to a different object of interest.

13. The method of claim 12, comprising providing feedback that a task cannot be completed or a resource is unavailable to complete the task.

14. The method of claim 12, wherein the robotic apparatus is configured to proceed to a location of the object of interest.

15. The method of claim 12, wherein the robotic apparatus is configured to obtain digitized images of an area surrounding the object of interest.

16. The method of claim 15, comprising processing data within the digitized images of the area surrounding the object of interest.

17. The method of claim 12, comprising tagging the object of interest with a tag and transmitting the tag to the robotic apparatus.

18. The method of claim 17, wherein an automated control system controls the robotic apparatus once the task and the object of interest are selected.

19. The method of claim 12, wherein the task is selection of a path that the robotic apparatus travels along.

20. The method of claim 5, further comprising a programmatic pairing link that pairs the input device with an attention block of the robotic apparatus, and further comprising a feedback indictor that confirms that the object of interest was received by the robotic apparatus.

* * * * *